United States Patent
Hansen et al.

(10) Patent No.: US 6,792,355 B2
(45) Date of Patent: Sep. 14, 2004

(54) METHODS FOR DETERMINING POLYPEPTIDE STRUCTURE, FUNCTION OR PHARMACOPHORE FROM COMPARISON OF POLYPEPTIDE SEQUENCES

(75) Inventors: Mark R. Hansen, San Diego, CA (US); Richard Kho, San Diego, CA (US); Hugo O. Villar, La Jolla, CA (US)

(73) Assignee: Triad Therapeutics, Inc., San Diego, CA (US)

( * ) Notice: Subject to any disclaimer, the term of this patent is extended or adjusted under 35 U.S.C. 154(b) by 40 days.

(21) Appl. No.: 10/032,395

(22) Filed: Dec. 21, 2001

(65) Prior Publication Data

US 2003/0134326 A1 Jul. 17, 2003

(51) Int. Cl.[7] ............................................... G06F 17/00
(52) U.S. Cl. ........................................... 702/19; 702/20
(58) Field of Search ..................................... 702/19, 20

(56) References Cited

PUBLICATIONS

Bejerano et al, Bioninformatics 17 (10), 927 (2001).*
Gerstein, M., "Measurements of the effectiveness of transitive sequences comparison, through a third 'intermediate' sequence," Bioinformatics, 14(8):707–717 (1998).
Altschul et al., "Basic Local Alignment Search Tool," J. Mol. Biol., 215:403–410 (1990).
Altschul et al., "Gapped BLAST and PSI–BLAST: a new generation of protein database search programs," Nucleic Acids Res., 25(17):3389–3402 (1997).
Apweiler et al., "Proteome Analysis Database: online application of InterPro and CluSTr for the functional classification of proteins in whole genomes," Nucleic Acids Res., 29(1)44–48 (2001).
Attwood et al., "PRINTS and PRINTS–S shed light on protein ancestry," Nucleic Acids Res., 30(1)239–241 (2002).
Bateman et al., "The Pfam Protein Families Database," Nucleic Acids Res., 30(1):276–280 (2002).
Bolten et al., "Clustering protein sequences–structure prediction by transitive homology,"Bioinformatics, 17(10):935–941 (2001).
Böhm, "The Computer Program LUDI: A New Method for the De Novo Design of Enzyme Inhibitors,"J. Comp. Aided Mol. Des., 6:61–78 (1992).
Carugo and Argos, "NADP–dependent Enzymes. I: Conserved Sterochemistry of Cofactor Binding," Proteins: Struc., Funct., Genet., 28:10–28 (1997).
Corpet et al;.., "ProDom and ProDom–CG: tools for protein domain analysis and whole genom comparisons," Nucleic Acids Res., 28(1):267–269 (2000).
Henikoff et al., "Increased coverage of protein families with the Blocks Database servers," Nucleic Acids Res., 28(1):228–230 (2000).
Hofmann et al., "The PROSITE database, its status in 1999," Nucleic Acids Res., 27(1):215–219 (1999).

Jarvis and Partick,"Clustering Using a Similarity Measure Based on Shared Near Neighbors," IEEE Trans. Comp., 22(11):1025–1034 (1973).
Manley, "Multivariate Statistical Methods, a Primer," Chapman Hall Chapter 8:100–113 (1994).
Murzin et al., "SCOP: A Structural Classification of Proteins Database for the Investigation of Sequences and Structures," J. Mol. Biol., 247:536–540 (1995).
Needleman and Wunsch, "A General Method and Applicable to the Search for Similarites in the Amino Acid Sequence of Two Proteins," J. Mol. Biol., 48:443–453 (1970).
Nicholas et al., "Strategies for Searching Sequence Database," BioTechniques, 28:1174–1191 (2000).
Pearson and Lipman, "Improved Tools for Biological Sequence Comparison," Proc. Natl. Acad. Sci. USA, 85:2444–2448 (1988).
Šali and Blundell, "Comparative Protein Modelling by Satisfaction of Spatial Restraints," J. Mol. Biol., 234:779–815 (1993).
Schnur, "Design and Diveristy Analysis of Large Combinatorial Libraries Using Cell–Based Methods," J. Chem. Inf. Comput. Sci., 39:36–45 (1999).
Sellers, "On the Theory and Computation of Evolutionary Distances," J. Appl. Math., 26(4):787–793 (1974).
Sellers, "Pattern Recognition in Genetic Sequences," Proc. Natl. Acad. Sci. USA, 76(7):3041 (1979).
Smith and Waterman, "Identification of Common Molecular Subsequences," J. Mol. Biol., 147:195–197 (1981).
Tatusova and Madden, "BLAST 2 Sequences, A New Tool for Comparing Protein and Nucleotide Sequences," FEMS Microbiol. Lett., 174:247–250 (1999).
Waterman and Eggert, "A New Algorithm for Best Subsequence Alignments with Application to tRNA–rRNA Comparisons," J. Mol. Biol., 197:723–728 (1987).
Worley et al., "Beauty–X: enhanced BLAST searches for DNA queries," Bioinformatics, 14(10):890–891 (1998).

* cited by examiner

Primary Examiner—James Martinell
(74) Attorney, Agent, or Firm—McDermott Will & Emery LLP

(57) ABSTRACT

The invention provides a method for separating two or more subsets of polypeptides within a set of polypeptides. The method includes the steps of: (a) determining a sequence comparison signature for each amino acid sequence in a set of amino acid sequences, wherein the sequence comparison signature includes pairwise comparison scores for the amino acid sequence compared to each of the other amino acid sequences in the set; (b) constructing a distance arrangement including the sequence comparison signatures related according to the distance between each of the sequence comparison signatures; and (c) identifying a first and second cluster of sequence comparison signatures in the distance arrangement, wherein the first cluster includes sequence comparison signatures for polypeptides having a similar protein fold or biological function, the protein fold or function being different compared to a protein fold or function of polypeptides having sequence comparison signatures in the second cluster.

82 Claims, 5 Drawing Sheets

| SEQUENCE | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | 9 | 0 | 0 | 0 | 0 | 0 | 0 | 0 | 0 | 5 | 2 | 1 | 0 | 0 | 0 |
| 2 | 0 | 9 | 1 | 6 | 3 | 0 | 3 | 1 | 0 | 0 | 0 | 0 | 0 | 0 | 0 |
| 3 | 0 | 1 | 9 | 4 | 4 | 0 | 5 | 1 | 0 | 0 | 0 | 0 | 0 | 0 | 0 |
| 4 | 0 | 6 | 4 | 9 | 3 | 0 | 1 | 2 | 0 | 0 | 0 | 0 | 0 | 0 | 0 |
| 5 | 0 | 3 | 4 | 3 | 9 | 0 | 3 | 7 | 0 | 0 | 0 | 0 | 0 | 0 | 0 |
| 6 | 0 | 0 | 0 | 0 | 0 | 9 | 0 | 1 | 1 | 0 | 0 | 0 | 2 | 3 | 1 |
| 7 | 0 | 3 | 5 | 1 | 3 | 0 | 9 | 3 | 0 | 0 | 0 | 0 | 0 | 0 | 0 |
| 8 | 0 | 1 | 1 | 2 | 7 | 0 | 3 | 9 | 0 | 0 | 0 | 0 | 0 | 0 | 0 |
| 9 | 0 | 0 | 0 | 0 | 0 | 1 | 0 | 0 | 9 | 0 | 0 | 0 | 2 | 4 | 3 |
| 10 | 5 | 0 | 0 | 0 | 0 | 0 | 0 | 0 | 0 | 9 | 1 | 3 | 0 | 0 | 0 |
| 11 | 2 | 0 | 0 | 0 | 0 | 0 | 0 | 0 | 0 | 1 | 9 | 2 | 0 | 0 | 0 |
| 12 | 1 | 0 | 0 | 0 | 0 | 0 | 0 | 0 | 0 | 3 | 2 | 9 | 0 | 0 | 0 |
| 13 | 0 | 0 | 0 | 0 | 0 | 2 | 0 | 0 | 2 | 0 | 0 | 0 | 9 | 6 | 5 |
| 14 | 0 | 0 | 0 | 0 | 0 | 3 | 0 | 0 | 4 | 0 | 0 | 0 | 6 | 9 | 1 |
| 15 | 0 | 0 | 0 | 0 | 0 | 1 | 0 | 0 | 3 | 0 | 0 | 0 | 5 | 1 | 9 |

FIGURE 1

| SEQUENCE | 1 | 12 | 11 | 10 | 8 | 7 | 4 | 3 | 2 | 5 | 6 | 14 | 13 | 9 | 15 |
|---|---|---|---|---|---|---|---|---|---|---|---|---|---|---|---|
| 1 | 9 | 1 | 2 | 5 | 0 | 0 | 0 | 0 | 0 | 0 | 0 | 0 | 0 | 0 | 0 |
| 12 | 1 | 9 | 2 | 3 | 0 | 0 | 0 | 0 | 0 | 0 | 0 | 0 | 0 | 0 | 0 |
| 11 | 2 | 2 | 9 | 1 | 0 | 0 | 0 | 0 | 0 | 0 | 0 | 0 | 0 | 0 | 0 |
| 10 | 5 | 3 | 1 | 9 | 0 | 0 | 0 | 0 | 0 | 0 | 0 | 0 | 0 | 0 | 0 |
| 8 | 0 | 0 | 0 | 0 | 9 | 3 | 2 | 1 | 1 | 7 | 0 | 0 | 0 | 0 | 0 |
| 7 | 0 | 0 | 0 | 0 | 3 | 9 | 1 | 5 | 3 | 3 | 0 | 0 | 0 | 0 | 0 |
| 4 | 0 | 0 | 0 | 0 | 2 | 1 | 9 | 4 | 6 | 3 | 0 | 0 | 0 | 0 | 0 |
| 3 | 0 | 0 | 0 | 0 | 1 | 5 | 4 | 9 | 1 | 4 | 0 | 0 | 0 | 0 | 0 |
| 2 | 0 | 0 | 0 | 0 | 1 | 3 | 6 | 1 | 9 | 3 | 0 | 0 | 0 | 0 | 0 |
| 5 | 0 | 0 | 0 | 0 | 7 | 3 | 3 | 4 | 3 | 9 | 0 | 0 | 0 | 0 | 0 |
| 6 | 0 | 0 | 0 | 0 | 0 | 0 | 0 | 0 | 0 | 0 | 9 | 3 | 2 | 1 | 1 |
| 14 | 0 | 0 | 0 | 0 | 0 | 0 | 0 | 0 | 0 | 0 | 3 | 9 | 6 | 4 | 1 |
| 13 | 0 | 0 | 0 | 0 | 0 | 0 | 0 | 0 | 0 | 0 | 2 | 6 | 9 | 2 | 5 |
| 9 | 0 | 0 | 0 | 0 | 0 | 0 | 0 | 0 | 0 | 0 | 1 | 4 | 2 | 9 | 3 |
| 15 | 0 | 0 | 0 | 0 | 0 | 0 | 0 | 0 | 0 | 0 | 1 | 1 | 5 | 3 | 9 |

FIGURE 2

| SEQUENCE | 1 | 12 | 11 | 10 | 8 | 7 | 4 | 3 | 2 | 5 | 6 | 14 | 13 | 9 | 15 |
|---|---|---|---|---|---|---|---|---|---|---|---|---|---|---|---|
| 1 | 9 | 1 | 2 | 5 | 0 | 0 | 0 | 0 | 0 | 0 | 0 | 0 | 0 | 0 | 0 |
| 12 | 1 | 9 | 2 | 3 | 0 | 0 | 0 | 0 | 0 | 0 | 0 | 0 | 0 | 0 | 0 |
| 11 | 2 | 2 | 9 | 1 | 0 | 0 | 0 | 0 | 0 | 0 | 0 | 0 | 0 | 0 | 0 |
| 10 | 5 | 3 | 1 | 9 | 0 | 0 | 0 | 0 | 0 | 0 | 0 | 0 | 0 | 0 | 0 |
| 8 | 0 | 0 | 0 | 0 | 9 | 3 | 2 | 1 | 1 | 7 | 0 | 0 | 0 | 0 | 0 |
| 7 | 0 | 0 | 0 | 0 | 3 | 9 | 1 | 5 | 3 | 3 | 0 | 0 | 0 | 0 | 0 |
| 4 | 0 | 0 | 0 | 0 | 2 | 1 | 9 | 4 | 6 | 3 | 0 | 0 | 0 | 0 | 0 |
| 3 | 0 | 0 | 0 | 0 | 1 | 5 | 4 | 9 | 1 | 4 | 0 | 0 | 0 | 0 | 0 |
| 2 | 0 | 0 | 0 | 0 | 1 | 3 | 6 | 1 | 9 | 3 | 0 | 0 | 0 | 0 | 0 |
| 5 | 0 | 0 | 0 | 0 | 7 | 3 | 3 | 4 | 3 | 9 | 0 | 0 | 0 | 0 | 0 |
| 6 | 0 | 0 | 0 | 0 | 0 | 0 | 0 | 0 | 0 | 0 | 9 | 3 | 2 | 1 | 1 |
| 14 | 0 | 0 | 0 | 0 | 0 | 0 | 0 | 0 | 0 | 0 | 3 | 9 | 6 | 4 | 1 |
| 13 | 0 | 0 | 0 | 0 | 0 | 0 | 0 | 0 | 0 | 0 | 2 | 6 | 9 | 2 | 5 |
| 9 | 0 | 0 | 0 | 0 | 0 | 0 | 0 | 0 | 0 | 0 | 1 | 4 | 2 | 9 | 3 |
| 15 | 0 | 0 | 0 | 0 | 0 | 0 | 0 | 0 | 0 | 0 | 1 | 1 | 5 | 3 | 9 |
| 16 | 0 | 0 | 0 | 0 | 1 | 3 | 6 | 0 | 3 | 4 | 0 | 0 | 1 | 0 | 0 |

FIGURE 3

```
1EBF_A                      STKVVNVAVIG-AGVVGSAFLDQLLAMKSTITYNLVLLAEAERSLISK--
sp|P45568|DXR_ECOLI_N-term  ---MKQLTILGSTGSIGCSTLDVVRHNPEHFRVVALVAGKNVTRMVEQCL
                               : :::.* :*:**  ..   :   ..  :: . :    ::

1EBF_A                      DFSPLNVGSDWKA---------ALAASTTKTLP-----------LDDL
sp|P45568|DXR_ECOLI_N-term  EFSPRYAVMDDEASAKLLKTMLQQQGSRTEVLSGQQAACDMAALEDVDQV
                            :***   .. ::            *  *::* .           * ::

1EBF_A                      IAHLKTSP---KPVILVDNTISSAYIAGFYTKFVENG---ISIATPNKKAFS
sp|P45568|DXR_ECOLI_N-term  MAAIVGAAGLLPTLAAIRAGKTILLANKESLVTCGRLFMDAVKQSKAQLL
                            :*    :   . : :: :* : *    *   . *        *

1EBF_A                      SDLATWKALFSNKPT---NGFVYHEATVGA
sp|P45568|DXR_ECOLI_N-term  PVDSEHNAIFQSLPQPIQHNLGYADLEQNG
                            .   :   *:  *    :*: :   :

FIGURE 4
```

METHODS FOR DETERMINING POLYPEPTIDE STRUCTURE, FUNCTION OR PHARMACOPHORE FROM COMPARISON OF POLYPEPTIDE SEQUENCES

BACKGROUND OF THE INVENTION

The present invention relates generally to classifying and identifying polypeptides having similar structure or function based on comparative amino acid sequence analysis and more specifically to determining structure-related properties of a ligand when bound to a polypeptide of known amino acid sequence.

Structure determination plays a central role in chemistry and biology due to the correlation between the structure of a molecule and its function. In particular, a three dimensional model of a therapeutic target polypepetide can be of valuable assistance in the design or discovery of therapeutic drugs. The structure of a ligand bound to a polypeptide as observed in a three dimensional model can be used as a template for identifying structural properties to be incorporated into candidate drugs. Alternatively, using computer assisted methods a candidate drug can be identified based on structural properties that allow docking to a binding site in the three dimensional model of the target polypeptide, much as a key fits a lock. By structure-based methods such as these, lead compounds can be identified for further development.

Although methods for structure determination are evolving, it is currently difficult, costly and time consuming to empirically determine the three dimensional structure of a polypeptide. In general, determining such structures for polypeptides complexed with ligands is even more difficult. One approach to circumventing this difficulty is theoretical modeling of polypeptide structures with or without a bound ligand based on more readily available structural and functional information. Such theoretical modeling approaches are based on the tenet that the three-dimensional structure and function of a polypeptide are imparted by its amino acid sequence and the corollary that polypeptides with similar amino acid sequences have similar structure and function.

Theoretical determination of a three dimensional model for a polypeptide by ab initio methods is a relatively undeveloped method. However, another theoretical approach, referred to as homology modeling, has been used to infer structure for a particular polypeptide by threading its amino acid sequence through or overlaying the sequence upon a three-dimensional model of a homologous polypeptide. The successful application of homology modeling to determining polypeptide structure relies upon choosing a correct polypeptide template for comparison. In most cases criteria for comparison are unavailable or unreliable.

Thus, there exists a need for efficient methods to identify homologous amino acid sequences and to identify structural or functional characteristics of a polypeptide based on its amino acid sequence. A need also exists for methods to determine ligand binding properties of polypeptides based on sequence information. The present invention satisfies these needs and provides related advantages as well.

SUMMARY OF THE INVENTION

The invention provides a method for separating two or more subsets of polypeptides within a set of polypeptides. The method includes the steps of: (a) determining a sequence comparison signature for each amino acid sequence in a set of amino acid sequences, wherein the sequence comparison signature includes pairwise comparison scores for the amino acid sequence compared to each of the other amino acid sequences in the set; (b) constructing a distance arrangement including the sequence comparison signatures related according to the distance between each of the sequence comparison signatures; and (c) identifying a first and second cluster of sequence comparison signatures in the distance arrangement, wherein the first cluster includes sequence comparison signatures for polypeptides having a similar protein fold or biological function, the protein fold or function being different compared to a protein fold or function of polypeptides having sequence comparison signatures in the second cluster.

The invention also provides a method for identifying a member of a polypeptide family. The method includes the steps of: (a) determining a query sequence comparison signature for an amino acid sequence, wherein the query sequence comparison signature inlcudes pairwise comparison scores for the amino acid sequence compared to each amino acid sequence in a set; (b) comparing the distance between the query sequence comparison signature and the sequence comparison signatures for other amino acid sequences in the set, wherein the sequence comparison signatures for other amino acid sequences in the set are clustered into polypeptide families; and (c) identifying a proximal cluster having one or more sequence comparison signatures that have a closer distance to the query sequence comparison signature than the sequence comparison signatures of a distal cluster, thereby identifying the polypeptide having the query sequence comparison signature as being a member of the polypeptide family for the proximal cluster.

BRIEF DESCRIPTION OF THE DRAWINGS

FIG. 1 shows a matrix of sequence comparison scores for 15 sequences.

FIG. 2 shows clustered sequence comparison scores for the 15 sequences presented in FIG. 1.

FIG. 3 shows a sequence comparison score for sequence 16 compared to the clustered sequence comparison scores presented in FIG. 2.

FIG. 4 shows a multiple alignment of $E.$ $Coli$ DXPR (SEQ ID NO:1) to $S.$ $aureas$ homoserine dehydrogenase (1EBF-A) (SEQ ID NO:2).

DETAILED DESCRIPTION OF THE INVENTION

Figure 5:
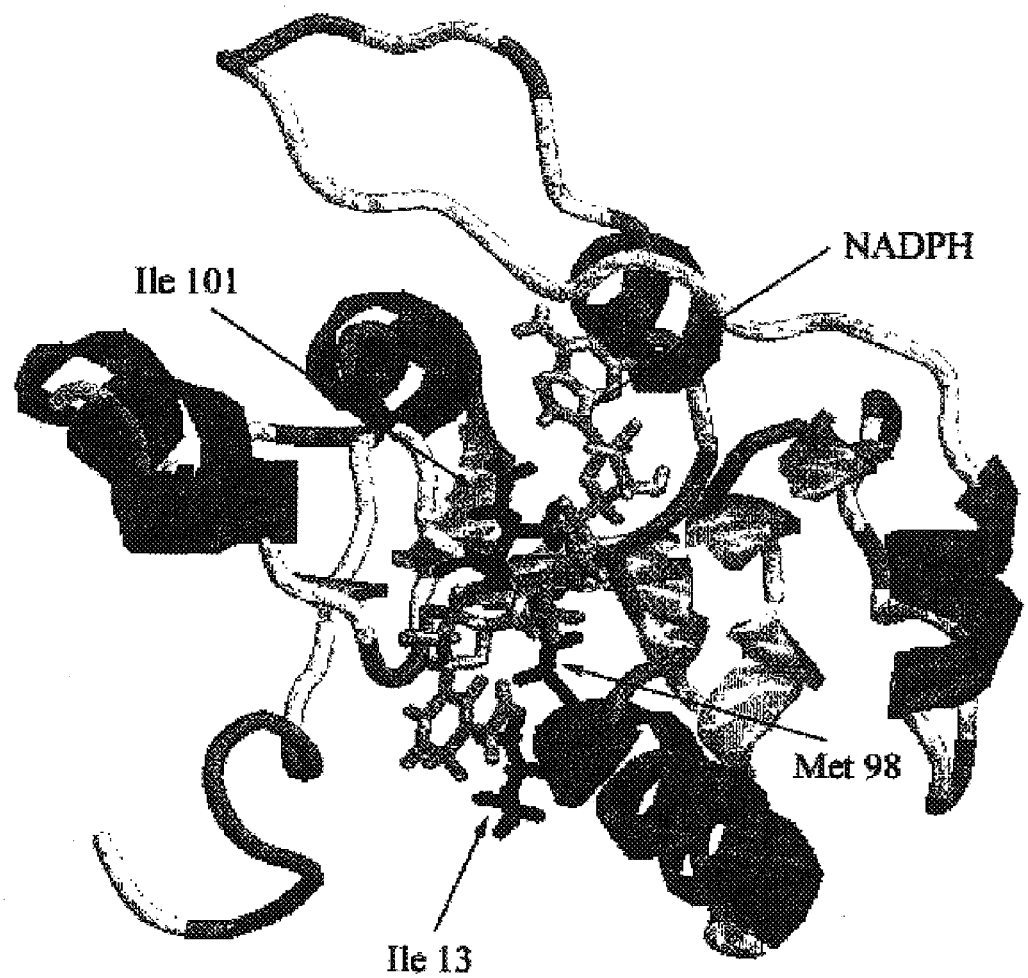
FIG. 5 shows a homology model for $E.$ $coli$ DXPR superimposed on the model of NAD+ from the X-ray crystal structure of $S.$ $aureas$ homoserine dehydrogenase.

The invention provides methods for classifying polypeptides into groups of similar structure or function based on amino acid sequence similarities. The methods can be used to classify polypeptides from a family of polypeptides that bind the same ligand, into pharmacofamilies that bind particular conformations of the ligand. An advantage of the invention is that ligand binding properties can be identified for polypeptides in a database for which sequence information is readily available but structural and/or functional properties are incompletely known or unavailable. An advantage of classifying polypeptides according to bound conformations of a ligand is that a pharmacofamily is likely to contain polypeptides having greater binding specificity for a particular molecule than other polypeptides in the same family. Thus, the methods allow identification of a pharmacofamily that can specifically interact with a particular therapeutic agent or drug.

Additionally, the methods of the invention can be used to determine a conformer model or pharmacophore model based on a bound conformation or conformation-dependent property of a ligand bound to polypeptides in a pharmacofamily. The invention is therefore advantageous in providing a model for the design and identification of therapeutic compounds having specificity for a pharmacofamily of polypeptides.

Another advantage of the invention is that the methods provide a correlation between polypeptide sequence, a parameter that is relatively easy to measure, and polypeptide function, polypeptide three-dimensional structure or bound-ligand three-dimensional structure, parameters of tremendous value but often difficult to measure. Therefore, the methods of the invention can be used to determine structural characteristics of a polypeptide or its bound ligand based on amino acid sequence of the polypeptide. Furthermore, the methods can be used to determine polypeptide function independent of three-dimensional structure information.

As used herein, the term "pharmacofamily," when used in reference to polypeptides, is intended to refer to a set of polypeptides that bind a ligand such that the ligand is bound in substantially the same conformation. As defined herein a "member" of a polypeptide pharmacofamily refers to an individual polypeptide that is classified in a polypeptide pharmacofamily because the polypeptide binds a conformation of a ligand that is substantially the same as a conformation of the ligand bound to another polypeptide in the pharmacofamily.

As used herein, the term "ligand-binding family" is intended to refer to a set of polypeptides that can bind to the same ligand, or portion thereof. The term includes a set of polypeptides having binding activity for a common ligand with sufficient affinity, avidity or specificity to allow measurement of the binding event. As defined herein, a "member" of a ligand-binding family refers to an individual polypeptide that binds the same ligand, or portion thereof, as that which binds another polypeptide in the ligand-binding family. The bound conformations of a ligand bound by individual members of a ligand-binding family can be substantially the same or different from each other.

As used herein, the term "bound conformation," when used in reference to a ligand, refers to the location of atoms of a ligand relative to each other in three dimensional space, where the ligand is bound to a polypeptide. The location of atoms in a ligand can be described, for example, according to bond angles, bond distances, relative locations of electron density, probable occupancy of atoms at points in space relative to each other, probable occupancy of electrons at points in space relative to each other or combinations thereof.

As used herein, the term "substantially the same," when used in reference to bound conformations of a ligand, or portion thereof, is intended to refer to two or more bound conformations that can be overlaid upon each other in 3 dimensional space such that all corresponding atoms between the two conformations are overlapped. Accordingly, "different" bound conformations cannot be overlaid upon each other in 3-dimensional space such that all corresponding atoms between the two bound conformations, or portion thereof, are overlapped. Structural overlap can be determined as described below.

As used herein, the term "sequence comparison signature" refers to a representation of the degree of similarity, likeness or identity for a particular amino acid sequence compared to a plurality of amino acid sequences. A representation included in the term can be a set of numerical representations such as pairwise comparison scores or a computer readable representation thereof. The numerical representations can be represented as a string of values and can be, for example, in a computer readable format. An amino acid sequence included in the term can be represented by nucleotide sequences or other sequence strings that can be translated into the amino acid sequence. A query sequence comparison signature is a sequence comparison signature that is compared to one or more other sequence comparison signatures in a set or database. A plurality of sequences included in the term can be 2 or more sequences. Larger pluralities can also be included such as those with 10 or more, 100 or more, 1000 or more, 2000 or more, 5000 or more or 10000 or more sequences.

As used herein, the term "pairwise comparison score" refers to a representation of the degree of similarity, likeness or identity for a particular amino acid sequence compared to another amino acid sequence. The representation can be a numerical value indicating a statistically relevant similarity between the sequence and the sequence model. Statistically relevant similarity is the probability that a score of a given value would be observed from the comparison of a random sequence to the length and composition of a query sequence and the sequences in a database. A statistically relevant similarity can be indicated by an expectation value (E-value), local sequence identity or bit score as described, for example, in Durbin et al., *Biological Sequence Analysis* Cambridge University Press (1998).

As used herein, the term "clustering" refers to partitioning a data set into two or more subsets where the members within each subset are similar and members in different subsets are correspondingly dissimilar. A data set included in the term can contain amino acid sequences, or representations of relationships between amino acid sequences such as sequence comparison signatures. The term can include partitioning polypeptides from a ligand-binding family into two or more pharmacofamilies. Partitioning can also be based on similarity or dissimilarity in other structural or functional properties such as protein fold, SCOP-family, enzymatic activity, presence or absence of a particular structural motif or other properties set forth below. The term can include partitioning based on sequence comparison scores or pairwise comparison scores. The term can include partitioning by, for example, hierarchical clustering such as agglomerative clustering or divisive clustering as described in Manley, *Multivariate Statistical Methods: a Primer*, Chapman and Hall, London (1995) and Aldenderfer and Blasfield, *Cluster Analysis*, Sage Publications, Beverley Hills (1984); non-hierarchical clustering such as Jarvis-Patrick clustering (see, for example, Jarvis and Patrick, *IEEE Trans. Comput.* C-22:1025–1034 (1973)); or cell-based clustering (see, for example, Schnur, *J. Chem. Inf. Comput. Sci.* 39:36–43 (1999)).

As used herein, the term "cluster" refers to a subset of amino acid sequences or representations thereof in a set that are similar to each other and different from amino acid sequences or representations thereof in another subset of the set.

As used herein, the term "distance" refers to a representation of the degree of difference or deviation that separates two things in relationship. The term can include the degree of difference or deviation that separates amino acid sequences according to an evolutionary model, structural properties such as Chou-Fasman propensities, chemical properties such as charge, polarity or shape or combinations thereof. The distance can be a measure of the separation of vector representations of sequences in high dimensional space. The distance can be, for example, a Euclidian distance, exclusive OR distance, Tanimoto coefficient or Mahalonobis distance.

As used herein, the term "distance arrangement" refers to a grouping of sequence comparison scores ordered relative to the degree of difference or deviation from each other. The term can include a graphical representation such as a matrix or tree structure.

As used herein, the term "polypeptide" is intended to refer to a polymer of two or more amino acids. The term is intended to include polymers containing amino acid sterioisomers, analogues and functional mimetics thereof. For example, derivatives can include chemical modifications of amino acids such as alkylation, acylation, carbamylation, iodination, or any modification which derivatizes the polypeptide. Analogues can include modified amino acids, for example, hydroxyproline or carboxyglutamate, and can include amino acids, or analogs thereof, that are not linked by peptide bonds. Mimetics encompass chemicals containing chemical moieties that mimic the function of the polypeptide regardless of the predicted three-dimensional structure of the compound. For example, if a polypeptide contains two charged chemical moieties in a functional domain, a mimetic places two charged chemical moieties in a spatial orientation and constrained structure so that the corresponding charge is maintained in three-dimensional space. Thus, all of these modifications are included within the term "polypeptide" so long as the polypeptide retains its binding function.

As used herein, the term "ligand" refers to a molecule that can specifically bind to a polypeptide. Specific binding, as it is used herein, refers to binding that is detectable over non-specific interactions by quantifiable assays well known in the art such as those that measure association rates, dissociation rates or equilibrium association or dissociation constants. A ligand can be essentially any type of natural or synthetic molecule including, for example, a polypeptide, nucleic acid, carbohydrate, lipid, amino acid, nucleotide or any organic derived compound. The term also encompasses a cofactor or a substrate of a polypeptide having enzymatic activity, or substrate that is inert to catalytic conversion by the bound polypeptide. Specific binding to a polypeptide can be due to covalent or non-covalent interactions.

As used herein, the term "conformer model" refers to a representation of points in a defined coordinate system wherein a point corresponds to a position of an atom in a bound conformation of a ligand. The coordinate system is preferably in 3 dimensions, however, manipulation or computation of a model can be performed in 2 dimensions or even 4 or more dimensions in cases where such methods are preferred. A point in the representation of points can, for example, correlate with the center of an atom. Additionally, a point in the representation of points can be incorporated into a line, plane or sphere to include a shape of one or more atom or volume occupied by one or more atom. A conformer model can be derived from 2 or more bound conformations of a ligand. For example a conformer model can be generated from 3 or more, 4 or more, 5 or more, 6 or more, 7 or more, 8 or more, 10 or more, 15 or more, 20 or more or 25 or more bound conformations of a ligand.

As used herein, the term "pharmacophore model" refers to a representation of points in a defined coordinate system wherein a point corresponds to a position or other characteristic of an atom or chemical moiety in a bound conformation of a ligand and/or an interacting polypeptide or ordered water. An ordered water is an observable water in a model derived from structural determination of a polypeptide. A pharmacophore model can include, for example, atoms of a bound conformation of a ligand, or portion thereof. A pharmacophore model can include both the bound conformations of a ligand, or portion thereof, and one or more atoms that both interact with the ligand and are from a bound polypeptide. Thus, in addition to geometric characteristics of a bound conformation of a ligand, a pharmacophore model can indicate other characteristics including, for example, charge or hydrophobicity of an atom or chemical moiety. A pharmacaphore model can incorporate internal interactions within the bound conformation of a ligand or interactions between a bound conformation of a ligand and a polypeptide or other receptor including, for example, van der Waals interactions, hydrogen bonds, ionic bonds, and hydrophobic interactions. A pharmacophore model can be derived from 2 or more bound conformations of a ligand. For example a conformer model can be generated from 3 or more, 4 or more, 5 or more, 6 or more, 7 or more, 8 or more, 10 or more, 15 or more, 20 or more or 25 or more bound conformations of a ligand.

A point in a pharmacophore model can, for example, correlate with the center of an atom or moiety. Additionally, a point in the representation of points can be incorporated into a line, plane or sphere to indicate a characteristic other than a center of an atom or moiety including, for example, shape of an atom or moiety or volume occupied by an atom or moiety. The coordinate system of a pharmacophore model is preferably in 3 dimensions, however, manipulation or computation of a model can be performed in 2 dimensions or even 4 or more dimensions in cases where such methods are preferred. Multidimensional coordinate systems in which a pharmacophore model can be represented include, for example, Cartesian coordinate systems, fractional coordinate systems, or reciprocal space. The term pharmacophore model is intended to encompass a conformer model.

As used herein, the term "conformation-dependent property," when used in reference to a ligand, refers to a characteristic of a ligand that specifically correlates with the three dimensional structure of a ligand or the orientation in space of selected atoms and bonds of the ligand. Thus, a ligand bound to a polypeptide in a distinct conformation will have at least one unique conformation-dependent property correlated with the bound conformation of the ligand. A conformation-dependent property can be derived from or include the entire ligand structure or selected atoms and bonds, including a fragment or portion of the complete atomic composition of the ligand. A conformation-dependent property that includes selected atoms and bonds of a ligand can include 2 or more, 3 or more, 5 or more, 10 or more, 15 or more, 20 or more, 25 or more, or 50 or more atoms of a bound conformation of a ligand.

A characteristic that specifically correlates with a three dimensional structure of a ligand is a characteristic that is substantially different between at least two different bound conformations of the same ligand and, therefore, distinguishes the two different bound conformations. A conformation-dependent property can include a physical or chemical characteristic of a ligand, for example, absorption and emission of heat, absorption and emission of electromagnetic radiation, rotation of polarized light, magnetic moment, spin state of electrons, or polarity. A conformation-dependent property can also include a structural characteristic of a ligand based, for example, on an X-ray diffraction pattern or a nuclear magnetic resonance (NMR) spectrum. A conformation-dependent property can additionally include a characteristic based on a structural model, for example, an electron density map, atomic coordinates, or x-ray structure. A conformation-dependent property can include a characteristic spectroscopic signal based on, for example, Raman, circular dichroism (CD), optical rotation, electron paramagnetic resonance (EPR), infrared (IR), ultraviolet/visible absorbance (UV/Vis), fluorescence, or luminescence spectroscopies. A conformation-dependent property can also include a characteristic NMR signal, for example, chemical shift, J coupling, dipolar coupling, cross-correlation, nuclear spin relaxation, transferred nuclear Overhauser effect, or combinations thereof. A conformation-dependent property can additionally include a thermodynamic or kinetic characteristic based on, for example, calorimetric measurement or binding affinity measurement. Furthermore, a conformation-dependent property can include characteristic based on electrical measurement, for example, voltammetry or conductance.

The invention provides a method for separating two or more subsets of polypeptides within a set of polypeptides. The method includes the steps of: (a) determining a sequence comparison signature for each amino acid sequence in a set of amino acid sequences, wherein the sequence comparison signature includes pairwise comparison scores for the amino acid sequence compared to each of the other amino acid sequences in the set; (b) constructing a distance arrangement including the sequence comparison signatures related according to the distance between each of the sequence comparison signatures; and (c) identifying a first and second cluster of sequence comparison signatures in the distance arrangement, wherein the first cluster includes sequence comparison signatures for polypeptides having a similar protein fold or biological function, the protein fold or function being different compared to a protein fold or function of polypeptides having sequence comparison signatures in the second cluster.

In a particular embodiment, the invention provides a method for identifying a polypeptide pharmacofamily. The method includes the steps of: (a) determining a sequence comparison signature for each amino acid sequence in a set of amino acid sequences, wherein the sequence comparison signature includes pairwise comparison scores for the amino acid sequence compared to each of the other amino acid sequences in the set; (b) constructing a distance arrangement including the sequence comparison signatures related according to the distance between each of the sequence comparison signatures; and (c) identifying separate clusters of sequence comparison signatures in the distance arrangement, wherein the separate clusters include sequence comparison signatures for sequences in the same ligand binding family and separate pharmacofamilies.

A set of amino acid sequences from which subsets of sequences can be identified in the methods can include polypeptides or proteins representing a wide range of structural or functional characteristics. A set of amino acid sequences need not have any particular predefined or known common characteristics. Such sequence sets include those found in genome or proteome databases from a particular organism or across a variety of organisms. Organism specific databases that can be used in the methods include FlyBase which contains sequences for the Drosophila melanogaster (The FlyBase consortium, *Nucl. Acids. Res.* 27:85–88 (1999)), the TB proteome (Cole et al., *Nature* 393:537–544 (1998)), or human genome (Venter et al., *Science* 291:1304–1351 (2001), Lander et al. *Nature* 409:860–921 (2001)). Examples of databases that include sequences from a wide diversity of organisms are Swiss-Prot (Bairoch et al., *Nucl. Acids. Res.* 28:45–48 (2000)), Protein Data Bank (PDB, operated by the Research Collaboratory for Structural Bioinformatics, see Berman et al., *Nucleic Acids Research*, 28:235–242 (2000)), Protein Information Resource (PIR; McGarvey et al., Bioinformatics 16:290–291 (2000)), PRF and TrEMBL (Bairoch et al., *Nucl. Acids. Res.* 28:45–48 (2000)).

The methods can also be used with a set of amino acid sequences that are preselected for a particular structural or functional characteristic. A preselected range of structural or functional characteristics for a set of polypeptides used in the methods can include, for example, binding to a particular ligand, interacting with a particular biological component such as another protein, common enzymatic function, common structural motifs or folds, common subcellular localization or co-expression due to a particular stimulus or developmental or growth stage. Those skilled in the art will be able to preselect a set of amino acid sequences based on that which is known for particular sequences as provided in the scientific literature or in annotations of particular databases. Examples of subsets of polypeptides from which subsets can be identified in the methods of the invention include, for example, kinases, G-protein coupled receptors, nuclear factors, proteases, dehydrogenases, phosphatases, transcription factors, nucleotide binding enzymes or membrane proteins.

Polypeptides of a set can be preselected for their ability to specifically bind to the same ligand, or portion thereof. Use of the methods with a set of amino acid sequences that is preselected for the ability to bind a particular ligand is demonstrated in Example II. Specific binding between a polypeptide and a ligand can be identified by methods known in the art. Methods of determining specific binding include, for example, equilibrium binding analysis, competition assays, and kinetic assays as described in Segel, *Enzyme Kinetics* John Wiley and Sons, New York (1975), and Kyte, *Mechanism in Protein Chemistry* Garland Pub. (1995). Thermodynamic and kinetic constants can be used to identify and compare polypeptides and ligands that specifically bind each other and include, for example, dissociation constant ($K_d$), association constant ($K_a$), Michaelis constant ($K_m$), inhibitor dissociation constant ($K_{is}$) association rate constant ($k_{on}$) or dissociation rate constant ($k_{off}$). For example, a family can be identified as having members that can specifically bind a ligand with a $K_d$ of at most $10^{-3}$ M, $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M or lower.

The use of a preselected set of amino acid sequences provides the advantage of narrowing the number of sequences to be compared thereby reducing computational demands for the methods. In addition, preselection can narrow the structural and functional diversity represented in the identified subsets to focus on desired characteristics. For example, a family of polypeptides known to bind a particular ligand can be used as a set in the methods thereby focusing the comparison on characteristics of ligand binding including the bound conformation of the ligand or the structure of the ligand binding site.

A set of amino acid sequences used in the methods can be translated from one or more nucleic acid sequences in a nucleic acid sequence database. Accordingly, the methods can include a step of translating the coding regions of a nucleic acid sequence into amino acid sequences. A coding region of a nucleic acid sequences can be translated according to the appropriate genetic code for the organism from which the nucleic acid sequence is derived. The coding region can be a predetermined portion of the sequence or in the case where exons and introns are present a predetermined set of spliced portions identified, for example, from annotations of the nucleic acid in the database. Alternatively, the coding region can be predicted or determined based on methods known in the art for predicting gene structure or coding sequence location. Computational methods for predicting the coding region of a nucleic acid sequence are known in the art as described in Pevzner, Computational Molecular Biolcay. an Algorithmic Approach, The MIT Press, Cambridge Mass. (2000), and include, for example, statistical approaches based on codon usage or in-frame hexamer count, similarity based approaches, spliced alignment approaches and Hidden Markov based approaches such as GENSCAN.

A nucleic acid sequence databases from which a set of amino acid sequences is translated can contain a variety of types of nucleic acids including, for example, genomic DNA sequences, cDNA sequences or mRNA sequences or combinations thereof. An example of a database including a variety of types of nucleic acid sequences is GenBank. Other nucleic acid sequence database useful in the methods include a genome database such as any of those described above.

A set of amino acid sequences used in the methods can include full protein sequences or fragments thereof. One or more amino acid sequence fragments present in a set of sequences used in the methods can correlate with particular exons or domains of a protein. An amino acid sequence fragment can also be translated from an Expressed Sequence Tag (EST). Thus the methods can be used to identify, classify or characterize proteins based on sequence fragments. For example, identification of a subset of polypeptides to which a translated EST sequence belongs can be used to predict the structure or function of the polypeptide encoded by the EST. Similarly, the methods can be used to identify, classify or characterize portions of proteins such as domains or exon encoded regions based on similar structure or function independent of the characteristics of other regions of the protein from which the fragment is derived.

Amino acid sequences in a set are compared in the methods on the basis of the sequence comparison signatures for each sequence. The sequence comparison signature can be any representation of the degree of similarity, likeness or identity for a particular amino acid sequence compared to the other amino acid sequences in the set. Such representations can include similarity scores calculated using any search algorithm or method of pairwise sequence comparison known by those skilled in the art such as those described below.

The dynamic programing algorithm is a mathematically rigorous method of pairwise sequence comparison and can be used according to several variants including, for example, Needleman-Wunsob (Needleman and Wunsch, J. Mol. Biol. 48:443–453(1970)), Sellers (Sellers, J. Appl. Math. 26:787–793(1974)), quasi-global alignment (Sellers Proc. Natl. Acad. Sci. USA 76:3041–3041 (1979)) and Smith-Waterman (Smith and Waterman, J. Mol. Biol. 147:195–197 (1981) and Waterman and Eggert, J. Mol. Biol. 197:723–728 (1987)). The dynamic programming algorithm is rigorous and therefore, well suited for finding optimum alignments and sequence comparison scores for a set of amino acid sequences. The dynamic programing algorithm, being rigorous is also computationally demanding. In applications of the methods in which large sequence sets are used or less rigorous comparison is required a heuristic search algorithm can be used.

Heuristic algorithms that can be used in the methods of the invention include, for example, BLAST and FASTA. BLAST, Basic Local Alignment Search Tool, uses a heuristic algorithm that reduces the computational requirements of the Smith-Waterman algorithm by seeking local alignments prior to comparing sequences in a restricted version of the Smith-Waterman algorithm. BLAST is therefore able to detect relationships among sequences including those which share only isolated regions of similarity including, for example, protein domains (Altschul et al., J. Mol. Biol. 215:403–410 (1990)). BLAST divides sequences into a list of overlapping words and extends the list to include all words that score above a predefined matrix-defined threshold. This threshold limits the number of matches that will be passed from the heuristic screening step to the comparison step. Those skilled in the art can use BLAST according to a default parameters as described by Tatiana et al., FEMS Microbial Lett. 174:247–250 (1999) or on the National Center for Biotechnology Information web page at ncbi.nlm.nih.gov/BLAsT/. Alternatively, parameters such as the length of the words, value of the predefined matrix-defined threshold or type of similarity matrix utilized can be adjusted to suit a particular application of the methods of the invention.

In addition to the originally described BLAST (Altschul et al., supra, 1990), modifications to the algorithm have been made (Altschul et al., *Nucleic Acids Res.* 25:3389–3402 (1997)). One modification is Gapped BLAST, which allows gaps, either insertions or deletions, to be introduced into alignments. Allowing gaps in alignments tends to reflect biologic relationships more closely. For example, gapped BLAST can be used to identify sequence identity within similar domains of two or more proteins. A second modification is PSI-BLAST, which is a sensitive way to search for sequence homologs. PSI-BLAST performs an initial Gapped BLAST search and uses information from any significant alignments to construct a position-specific score matrix, which replaces the query sequence for the next round of database searching. A PSI-BLAST search is often more sensitive to weak but biologically relevant sequence similarities.

FASTA uses a word search algorithm as a heuristic screen prior to performing a restricted Smith-Waterman alignment (Pearson and Lippman, Proc. Natl. Acad. Sci. USA 85:2444–2448 (1988)). In the word search both the query and library sequences are divided into overalapping words of specified length. The lists of words for the query and library sequences are compared in a matrix and the diagonal with the most matching words is taken as the region most likely to contain the best alignment. The results from the word search are used to identify sequences with sufficient similarity to use in the subsequent alignment step. Those skilled in the art can use default parameters or adjust parameters such as word size, window size for defining the length of insertions or deletions one sequence can accumulate relative to another or the type of similarity matrix utilized.

A similarity matrix used in a sequence comparison algorithm can be any that quantifies the probability that a particular substitution of one amino acid for another will preserve or disrupt the physical and chemical properties necessary to the structure or function of the polypeptide. Similarity matrices can be based on evolutionary models; structural properties such as Chou-Fasman propensities; chemical properties such as charge, shape, or polarity; and combinations thereof. Examples of similarity matrices known in the art and useful in the invention include the PAM matrix and BLOSUM matrix as described in Nicholas et al., *Biotechniques,* 28:1174–1191 (2000). In addition, the scale of the similarity matrix used in the comparison algorithm can be adjusted to suit the set of amino acids being compared or the resulting range of percent identity. Examples of differently scaled matrices that can be used in the methods of the invention include PAM40, PAM120, PAM240, BLOSUM60, BLOSUM40 and BLOSUM30 as described, for example, in Nicholas et al., supra (2000).

Once similarity scores have been determined for an amino acid sequence compared to the other sequences in a set, a sequence comparison signature containing these scores can be created. A sequence comparison signature of the invention can include any of a variety of known comparison scores including scores provided by the above-described algorithms such as E-scores, sequence identity scores or Bit-scores. These scores can be binned into representation such as a string of values as described in Example I.

The methods can include a step of converting sequence similarity scores by a uniform transformation. Any uniform transformation capable of converting the sequence similarity scores or the sequence comparison signatures in which they reside into a format amenable to comparison and clustering can be used in the methods of the invention. For example, a pairwise similarity score can be converted to a binary score indicating presence or absence of similarity between the two sequences being compared. Assignment of a binary score can be determined by a predefined percent identity cutoff where two sequences having a percent identity below the cutoff value are assigned a score of 0 indicating absence of similarity and 2 sequences having a percent identity above the cutoff are assigned a score of 1 indicating presence of similarity. Adjustment of the cutoff value can be used to alter the sensitivity and selectivity of the methods. In particular, as the cutoff is increased sensitivity is reduced, due to the reduction in the number of related sequences identified, and selectivity is increased due to the decrease in the number of unrelated sequences identified as being similar. Sequence similarity scores can also be binned according to particular ranges of identity or similarity as demonstrated in Example I where sequence similarity scores are binned into 10 groups.

Conversion of sequence similarity scores with a uniform transformation can include a mathematical manipulation such as an inverse function (for example, 1/score), an exponential function (for example, $e^{-score}$) or an inverse of an exponential (for example, $1/10^{score}$). Another conversion useful in the methods is a hashing algorithm which can be used to generate a hashkey from the sequence comparison scores. A hashkey is a compact numerical representation used to solve indexing problems as described in Pieprzyk and Sadeghiyan, "Design of Hashing Algorithms" *Lecture Notes in Computer Science*, Vol. 756 Springer-Verlag (1993). A hashkey can be used to assign a memory address to a sequence similarity score or its vector, thereby reducing computation time required for clustering.

A set of sequence similarity signatures that have been determined for a set of proteins can be related to each other according to the distance separating each sequence similarity signature from the other. A convenient representation for relating sequence similarity signatures is points in space. A sequence similarity signature can be represented in high dimensional space as a vector, where each pairwise distance value, or converted value thereof, is a point in each coordinate of the space. Proximity of the points in this space indicates similarity, whereas points that are distal are dissimilar.

The distance between two similarity signatures, that are represented as a first and second vector in high dimensional space, can be determined based on the distances separating the points of the first vector from the points of the second vector. A variety of distance measures are known in the art can be used in the methods of the invention including, for example, Euclidian distance. Euclidian distance is the square root of the sum of the difference between each of the elements in the two compared vectors, squared. Another distance is the Mahalanobis distance, which scales the difference in each coordinate by the inverse of the variance in that dimension as described, for example, in Mahalanobis, Proc. Natl. Acad. Sci. USA 12:49–55 (1936). The cosine of the angle between the two vectors can also be computed and used as a distance metric. Hamming distance between two vectors is also useful in the methods of the invention and it is given by the count of the number of elements in which the two vectors differ.

Distances that are particularly useful when binary sequence comparison scores are used include, for example, the exclusive OR which is a reduction of a hamming distance to a binary case, again being a count of the number of elements differing between the two vectors that are compared. The Tanimoto coefficient is the ratio of bits set (where a bit set is a bit that is equal to 1) for both vectors to the total number of bits set in either vector. A generalization of the Tanimoto coefficient is the Tversky Similarity, where both vectors can be given different weighting as described in Sneath and Sokal, Numerical Taxonomy WH Freeman, San Francisco (1973). Those skilled in the art will recognize that this is only a partial list of the methods known in the art for measuring distance between vectors and will be able to use other known methods for measuring distance between vectors in the methods to determine the distance between sequence similarity signatures according to the teaching herein.

In addition to the distance arrangements set forth above, a variety of other formats that are convenient for comparing distances can also be used including, for example, a matrix as described in Example I or tree structure as described in Durbin et al., supra (1998).

Once a distance arrangement has been created, sequence comparison signatures within predefined distances can be grouped using a clustering algorithm including, for example, a hierarchical clustering algorithm such as a agglomerative or divisive hierarchical clustering algorithm (see, for example, Kaufman and Rousseeuw, *Finding Groups in Data: An introduction to Cluster Analysis* John Wiley and Sons, New York (1990)). A non-hierarchical clustering algorithm can also be used such as the Jarvis-Patrick algorithm (Jarvis and Patrick, *IEEE Trans. Comput.* C-22:1025–1034 (1973)). The Jarvis-Patrick algorithm clusters sequence similarity signatures according to the number of nearest neighbors. Although the determination of which points are neighbors is dependent upon the distance between neighbors, clustering by the Jarvis-Patrick algorithm is not based solely on distance. Clustering can also be achieved with a cell-based clustering algorithm (see, for example, Schnur, *J. Chem. Inf. Comput. Sci.* 39:36–43 (1999)). Cell-based clustering divides the space containing sequence similarity signatures into areas or volumes and clusters those that fall into the same volume. The cell-based method is not based solely on distance since points that are separated by a cell division although quite proximal can be separated into different clusters. Clustering in cell-based methods is dependent upon the size and shape of the cells which can be adjusted to alter the number of clusters identified or range of similarity of sequences in each cluster to suit a particular application of the method.

Clusters that have been created based on sequence scores can be evaluated to identify subsets of polypeptides having one or more common structural or functional characteristics. Such an evaluation can be used to confirm membership of a polypeptide in a particular subset or to determine membership for a polypeptide that is apparently similar to clusters for more than one subset. The structural and functional similarities can be any that are encoded by the amino acid sequences of the polypeptides identified. Structural similarities of subsets identified by the methods can include, for example, similar protein fold such as those present in particular SCOP families (Murzin et al., *J. Mol. Biol.* 247:536–540 (1995)). The subgroups identified by the methods can have similar overall protein fold or regions of similar fold such as domains, active sites or binding sites.

Protein fold refers to the specific geometric arrangement and connectivity of a combination of secondary structure elements in a polypeptide structure. Secondary structure elements of a polypeptide that can be arranged into a fold including, for example, alpha helices, beta sheets, turns and loops are well known in the art. Folds of a polypeptide can be recognized by one skilled in the art and are described in, for example, Branden and Tooze, *Introduction to protein structure*, Garland Publishing, New York (1991) and Richardson, *Adv. Prot. Chem.* 34:167–339 (1981). An example of a ligand-binding family of polypeptides having members with different folds is the NAD(P) binding polypeptides within which the folds include, for example, the NAD(P)(H) binding Rossman fold, heme-linked catalase fold, β-α TIM barrel fold, dihydrofolate reductase fold, FAD/NAD(P)(H) binding domain fold and the ferrodoxin like fold as described in U.S. patent application Ser. No. 09/753,020, which is hereby incorporated by reference.

The methods can be used to identify polypeptide subsets containing members that share one or more characteristics other than common three-dimensional structure, protein fold or SCOP family membership. In particular, some polypeptides are known to have similar protein fold or to be classified into the same SCOP family but to have different functions. An advantage of the invention is that subsets can be identified based on similarities in function that are not immediately apparent from structural similarity or even pairwise sequence comparison. In addition, the methods can be used to identify a member of a subset of sequences based on one or more common characteristics other than three-dimensional structure, protein fold or SCOP family membership, the common characteristics including, for example, functional similarities. Functional similarities of subsets of polypeptides identified by the methods can include, for example, binding to a common ligand, similar enzymatic activity or similar subcellular localization. Use of the methods to identify subsets of polypeptides having similar enzyme function are demonstrated in Example II where subsets within the family of NAD(P)(H) binding polypeptides are identified including, for example, the dehydrogenases, reductases, isomerases, oxidases, catalases, synthases, cyclases, transferases, glucosidases and galactosidases listed in Table 1. Pharmacofamilies containing members that bind to substantially the same bound conformation of a ligand can also be identified by evaluating clustered polypeptides based on the structures of bound ligands. Use of the methods to identify pharmacofamilies that bind to a common pharmacophore is also demonstrated in Example II.

The methods of the invention can be used to identify any number of pharmacofamilies in a family up to and including the number of different bound conformations of a ligand that can be distinguished in the family. In cases where two or more polypeptide pharmacofamilies reside in a polypeptide family, clusters containing different pharmacofamilies can be distinguished according to differences in bound conformations of a ligand bound to the polypeptides. In this case, a bound conformation of a ligand can be determined and compared according to the methods described below. Polypeptides bound to different bound conformations of a ligand can be identified as those that do not show substantial overlap of all corresponding atoms when bound conformations are overlaid. Thus, polypeptides that bind different bound conformations of a ligand can be separated into different pharmacofamilies. Pharmacofamilies in turn can be identified as containing polypeptides that bind substantially the same bound conformation of a ligand.

A bound conformation of a ligand bound to a polypeptide can be determined from a previously observed molecular structure or from data specifying a molecular structure for a bound conformation of a ligand. Previously observed structures can be acquired for use in the invention by searching a database of existing structures. An example of a database that includes structures of bound conformations of ligands bound to polypeptides is the Protein Data Bank (PDB, operated by the Research Collaboratory for Structural Bioinformatics, see Berman et al., *Nucleic Acids Research,* 28:235–242 (2000)). A database can be searched, for example, by querying based on chemical property information or on structural information. In the latter approach, an algorithm based on finding a match to a template can be used as described, for example, in Martin, "Database Searching in Drug Design," *J. Med. Chem.* 35:2145–2154 (1992).

A bound conformation of a ligand bound to a polypeptide can be determined from an empirical measurement, or from a database. Data specifying a structure can be acquired using any method available in the art for structural determination of a ligand bound to a polypeptide. For example, X-ray crystallography can be performed with a crystallized complex of a polypeptide and ligand to determine a bound conformation of the ligand bound to the polypeptide. Methods for obtaining such crystal complexes and determining structures from them are well known in the art as described for example in McRee et al., *Practical Protein Crystallography*, Academic Press, San Diego 1993; Stout and Jensen, X-ray *Structure Determination: A practical guide*, $2^{nd}$ Ed. Wiley, New York (1989); and McPherson, *The Preparation and Analysis of Protein Crystals*, Wiley, New York (1982). Another method useful for determining a bound conformation of a ligand bound to a polypeptide is Nuclear Magnetic Resonance (NMR). NMR methods are well known in the art and include those described for example in Reid, *Protein NMR Techniques*, Humana Press, Totowa N.J. (1997); and Cavanaugh et al., *Protein NMR Spectroscopy: Principles and Practice*, ch. 7, Academic Press, San Diego Calif. (1996).

A bound conformation of a ligand can also be determined from a hypothetical model. For example, a hypothetical model of a bound conformation of a ligand can be produced using an algorithm which docks a ligand to a polypeptide of known structure and fits the ligand to the polypeptide binding site. Algorithms available in the art for fitting a ligand structure to a polypeptide binding site include, for example, DOCK (Kuntz et al., *J. Mol. Biol.* 161:269–288 (1982)) and INSIGHT98 (Molecular Simulations Inc., San Diego, Calif.).

Common structural properties can be identified by comparing the three dimensional structures of two or more polypeptides or a bound ligand using methods known in the art including, for example, cluster analysis of structures, visual inspection and pairwise structural comparisons. Cluster analysis of structures is commonly performed by, but not limited to, partitioning methods or hierarchical methods as described, for example, in Kauffman and Rousseeuw, Finding Groups in Data: An Introduction to Cluster Analysis, John Wiley and Sons Inc., New York (1990). Partitioning methods that can be used include, for example, partitioning around medoids, clustering large applications, and fuzzy analysis, as described in Kauffman and Rousseeuw, supra. Hierarchical methods useful in the invention include, for example, agglomerative nesting, divisive analysis, and monothetic analysis, as described in Kauffman and Rousseeuw, supra. Algorithms for cluster analysis of molecular structures are known in the art and include, for example, COMPARE (Chiron Corp. 1995; distributed by Quantum Chemistry program Exchange, Indianapolis Ind.). COMPARE can be used to make all possible pairwise comparisons between a set of conformations of polypeptides or bound ligands or portions thereof. COMPARE reads PDB files and uses a Ferro-Hermanne ORIENT algorithm for a least squares root mean square (RMS) fit. The structures can be clustered into groups using the Jarvis-Patrick nearest neighbors algorithm. Based on the RMS deviation between polypeptide structures or bound conformations of a ligand, or portions thereof, a list of 'nearest neighbors' for each structure is generated. Two structures are then grouped together or clustered if: (1) the RMS deviation is sufficiently small and (2) if both structures share a determined number of common 'neighbors'. Both criteria are adjusted by the program to generate clusters based on a user defined cutoff for distance between individual clusters. Follow up analysis can be conducted using InsightII to verify structural clusters. Thus, two or more polypeptides can be confirmed as being in the same cluster or a polypeptide can be assigned to one of two or more proximal clusters based on common cluster assignment evaluated by both sequence based clustering and structure-based clustering.

Structural similarity can also be identified by overlaying two or more structures to determine a degree of overlap. For example, two structures can be compared based on the proximity of centroid position for each atom using known algorithms such as the OVERLAY routine in INSIGHT98 (Molecular Simulations Inc., San Diego Calif.). The degree of overlap can be determined based on root mean square deviation as described below. Two or more structures that show substantial similarity in structural overlap can be used to produce an average structure. The averaged structure can, in turn, be used as a template for comparing a polypeptide structure or bound conformation of a ligand to determine membership in a subset or pharmacofamily. Methods for comparing bound conformations of a ligand and producing an average structure are described in U.S. patent application Ser. No. 09/753,020, which is hereby incorporated by reference.

Using methods such as those described above, one skilled in the art will know how to identify structures that are substantially the same. For example, similarity can be evaluated according to the goodness of fit between two or more three-dimensional models of a polypeptide or bound ligand, or fragments thereof. Goodness of fit can be represented by a variety of parameters known in the art including, for example, the root mean square deviation (RMSD). A lower RMSD between structures correlates with a better fit compared to a higher RMSD between structures (see for example, Doucet and Weber, ComDuter-Aided Molecular Design: Theory and Applications, Academic Press, San Diego, Calif. (1996)). Polypeptides having substantially the same structures can be identified by comparing mean RMSD values for the backbones of the polypeptides. Polypeptides, or fragments thereof, having substantially the same structures can have a mean backbone RMSD compared to each other that is less than about 5 Å or less than about 3 Å. Those skilled in the art will know that despite a high RMSD between overall structures indicating overall structural differences, two polypeptides can contain domains or other regions that are similar. Thus, a model used in comparing polypeptide structures can be that of the backbone structure of a domain or other region of the polypeptide. Bound conformations of a ligand having substantially the same structures can have a mean RIVISD compared to each other that is less than about 1.1 Å.

The subset or pharmacofamily to which an apparently clustered polypeptide belongs can also be identified by comparing the RMSD for its structure or for the bound conformation of its ligand to the structures of members in multiple clusters. Using this value for comparison, a member polypeptide is identified as having a smaller RMSD when compared to the coordinates of one or more structures within its subset or pharmacofamily than when compared to the coordinates of one or more structures in another subset or pharmacofamily. In addition, a member of a subset or pharmacofamily can be identified as having an RMSD compared to one or more polypeptide or ligand structures of the members in the subset or pharmacofamily that are smaller than the RMSD between the average coordinates of the polypeptide or ligand structures in each cluster.

In addition, bound conformations of a ligand can be compared with respect to dihedral angles at particular bonds. Comparison between dihedral angles can be used, for example, in combination with overall RMSD comparisons such as those described above. Therefore, bound conformations that are not easily distinguished by comparison of overall RMSD alone, can be distinguished according to the combined comparison of RMSD and dihedral angle. Bound conformations of a ligand that are bound to members of different pharmacofamilies can have dihedral angles that differ, for example, by at least about 10 degrees, 30 degrees, 45 degrees, 90 degrees or 180 degrees.

A molecular structure can be conveniently stored and manipulated using structural coordinates. Structural coordinates can occur in any format known in the art so long as the format can provide an accurate reproduction of the observed structure. For example, crystal coordinates can occur in a variety of file types including, for example, .fin, .df, .phs, or .pdb as described for example in McRee, supra. One skilled in the art will recognize that structural coordinates can be derived from any method known in the art to determine the structure of a polypeptide or bound ligand including, for example, X-ray crystallographic analysis or NMR spectroscopy.

Structures at atomic level resolution can be useful in the methods of the invention. Resolution, when used to describe molecular structures, refers to the minimum distance that can be resolved in the observed structure. Thus, resolution where individual atoms can be resolved is referred to in the art as atomic resolution. Resolution is commonly reported as a numerical value in units of Angstroms (Å, $10^{-10}$ meter) correlated with the minimum distance which can be resolved such that smaller values indicate higher resolution. Structural models useful in the methods of the invention can have a resolution better than about 10 Å, 5 Å, 3 Å, 2.5 Å, 2.0 Å, 1.5 Å, 1.0 Å, 0.8 Å, 0.6 Å, 0.4 Å, or about 0.2 Å or better. Resolution can also be reported as an all atom RMSD as used, for example, in reporting NMR data. Bound conformations of a ligand useful in the methods of the invention can have an all atom RMSD better than about 10 Å, 5 Å, 3 Å, 2.5 Å, 2.0 Å, 1.5 Å, 1.0 Å, 0.8 Å, 0.6 Å, 0.4 Å, or about 0.2 Å or better.

Any representation that correlates with the structure of a molecule can be used in the methods of the invention. For example, a convenient and commonly used representation is a displayed image of the structure. Displayed images that are particularly useful for determining the structure of a polypepetide or a bound conformation of a ligand include, for example, ball and stick models, density maps, space filling models, surface map, Connolly surfaces, Van der Waals surfaces or CPK models. Display of images as a computer output, for example, on a video screen can be advantageous for the structural overlay and clustering methods described herein.

The invention can be used with any ligand that binds to two or more different polypeptides having different sequences including, for example, chemical or biological molecules such as simple or complex organic molecules, metal-containing compounds, carbohydrates, peptides, peptidomimetics, carbohydrates, lipids, nucleic acids, and the like.

In one embodiment, the methods of the invention can be used with a ligand that is a nucleotide derivative including, for example, a nicotinamide adenine dinucleotide-related molecule. Nicotinamide adenine dinucleotide-related (NAD-related) molecules that can be used in the methods of the invention can be selected from the group consisting of oxidized nicotinamide adenine dinucleotide (NADI$^+$), reduced nicotinamide adenine dinucleotide (NADH), oxidized nicotinamide adenine dinucleotide phosphate (NADP$^+$), and reduced nicotinamide adenine dinucleotide phosphate (NADPH). An NAD-related molecule can also be a mimetic of the above-described molecules.

In another embodiment, the methods of the invention can be used with a ligand that is an adenosine phosphate-related molecule. Adenosine phosphate-related molecules can be selected from the group consisting of adenosine triphosphate (ATP), adenosine diphosphate (ADP), adenosine monophosphate (AMP), and cyclic adenosine monophosphate (cAMP). An adenosine phophate-related molecule can also be a mimetic of the above-described molecules. A mimetic of an adenosine phosphate-related molecule that can be used in the invention includes, for example, quercetin, adenylylimidodiphosphate (AMP-PNP) or olomoucine.

A ligand useful in the methods of the invention can be a cofactor, coenzyme or vitamin including, for example, NAD, NADP, or ATP as described above. Other examples include thiamine (vitamin $B_1$), riboflavin (vitamin $B_2$), pyridoximine (vitamin B6), cobalamin (vitamin $B_{12}$), pyrophosphate, flavin adenine dinucleotide (FAD), flavin mononucleotide (FMN), pyridoxal phosphate, coenzyme A, ascorbate (vitamin C), niacin, biotin, heme, porphyrin, folate, tetrahydrofolate, nucleotide such as guanosine triphosphate, cytidine triphosphate, thymidine triphosphate, uridine triphosphate, retinol (vitamin A), calciferol (vitamin $D_2$), ubiquinone, ubiquitin, α-tocopherol (vitamin E), farnesyl, geranylgeranyl, pterin, pteridine or S-adenosyl methionine (SAM).

A polypeptide can be used as a ligand in the invention. For example, a ligand can be a naturally occurring polypeptide ligand such as a ubiquitin or polypeptide hormone including, for example, insulin, human growth hormone, thyrotropin releasing hormone, adrenocorticotropic hormone, parathyroid hormone, follicle stimulating hormone, thyroid stimulating hormone, luteinizing hormone, human chorionic gonadotropin, epidermal growth factor, nerve growth factor and the like. In addition a polypeptide ligand can be a non-naturally occurring polypeptide that has binding activity. Such polypeptide ligands can be identified, for example, by screening a synthetic polypeptide library such as a phage display library or combinatorial polypeptide library as described below. A polypeptide ligand can also contain amino acid analogs or derivatives such as those described below. Methods of isolation of a polypeptide ligand are well known in the art and are described, for example, in Scopes, *Protein Purification: Principles and Practice*, 3$^{rd}$ Ed., Springer-Verlag, New York (1994); Duetscher, *Methods in Enzymology*, Vol 182, Academic Press, San Diego (1990); and Coligan et al., *Current protocols in Protein Science*, John Wiley and Sons, Baltimore, Md. (2000).

A nucleic acid can also be used as a ligand in the invention. Examples of nucleic acid ligands useful in the invention include DNA, such as genomic DNA or cDNA or RNA such as mRNA, ribosomal RNA or tRNA. A nucleic acid ligand can also be a synthetic oligonucleotide. Such ligands can be identified by screening a random oligonucleotide library for ligand binding activity, for example, as described below. Nucleic acid ligands can also be isolated from a natural source or produced in a recombinant system using well known methods in the art including, for example, those described in Sambrook et al., *Molecular Cloning: A Laboratory Manual*, 2nd ed., Cold Spring Harbor Press, Plainview, N.Y. (1989); Ausubel et al., *Current Protocols in Molecular Biology* (Supplement 47), John Wiley & Sons, New York (1999).

A ligand used in the invention can be an amino acid, amino acid analog or derivatized amino acid. An amino acid ligand can be one of the 20 essential amino acids or any other amino acid isolated from a natural source. Amino acid analogs useful in the invention include, for example, neurotransmitters such as gamma amino butyric acid, serotonin, dopamine, or norepenephrine or hormones such as thyroxine, epinephrine or melatonin. A synthetic amino acid, or analog thereof, can also be used in the invention. A synthetic amino acid can include chemical modifications of an amino acid such as alkylation, acylation, carbamylation, iodination, or any modification that derivatizes the amino acid. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Naturally occurring amino acid derivatives of the twenty standard amino acids can also be included in a cluster of bound conformations including, for example, 4-hydroxyproline, 5-hydroxylysine, 3-methylhistidine, homoserine, ornithine or carboxyglutamate.

A lipid ligand can also be used in the invention. Examples of lipid ligands include triglycerides, phospholipids, glycolipids or steroids. Steroids useful in the invention include, for example, glucocorticoids, mineralocorticoids, androgens, estrogens or progestins.

Another type of ligand that can be used in the invention is a carbohydrate. A carbohydrate ligand can be a monosaccharide such as glucose, fructose, ribose, glyceraldehyde, or erythrose; a disaccharide such as lactose, sucrose, or maltose; oligosaccharide such as those recognized by lectins such as agglutinin, peanut lectin or phytohemagglutinin, or a polysaccharide such as cellulose, chitin, or glycogen.

Once two or more subsets of polypeptides have been identified in a particular set of amino acid sequences, another sequence can be compared to the set to identify to which subset the sequence belongs. Therefore, the invention provides a method for identifying a subset of polypeptides. The method includes the steps of: (a) determining a query sequence comparison signature for an amino acid sequence, wherein the query sequence comparison signature includes pairwise comparison scores for the amino acid sequence compared to each amino acid sequence in a set; (b) comparing the distance between the query sequence comparison signature and the sequence comparison signatures for other amino acid sequences in the set, wherein the sequence comparison signatures for other amino acid sequences in the set are clustered into two or more subsets; and (c) identifying a proximal cluster having one or more sequence comparison signature that has a closer distance to the query sequence comparison signature than the sequence comparison signatures of a distal cluster.

A similar method can be used to identify a member of a pharmacofamily. The method includes the steps of: (a) determining a query sequence comparison signature for an amino acid sequence, wherein the query sequence comparison signature includes pairwise comparison scores for the amino acid sequence compared to each amino acid sequence in a set; (b) comparing the distance between the query sequence comparison signature and the sequence comparison signatures for other amino acid sequences in the set, wherein the sequence comparison signatures for other amino acid sequences in the set are clustered into pharmacofamilies; and (c) identifying a proximal cluster having one or more sequence comparison signature that has a closer distance to the query sequence comparison signature than the sequence comparison signatures of a distal cluster, thereby identifying the sequences having the query sequence comparison signature as being a member of the pharmacofamily for the proximal cluster, wherein the pharmacofamilies for the proximal and distal clusters belong to the same ligand binding family.

Further provided by the invention is a method for constructing a conformer model. The method includes the steps of: (a) determining a sequence comparison signature for each amino acid sequence in a set of amino acid sequences, wherein the sequence comparison signature includes pairwise comparison scores for the amino acid sequence compared to each of the other amino acid sequences in the set; (b) constructing a distance arrangement including the sequence comparison signatures related according to the distance between each of the sequence comparison signatures; (c) identifying separate clusters of sequence comparison signatures in the distance arrangement, wherein the separate clusters include sequence comparison signatures for amino acid sequences in the same ligand binding family and separate pharmacofamilies; (d) determining bound conformations of the ligand bound to the members of a pharmacofamily; and (e) constructing an average structure of the bound conformations, wherein the average structure is a conformer model of the ligand.

An average structure of the bound conformations of a ligand in a cluster can be determined by a variety of methods known in the art. For example, an average structure can be determined by overlaying bound conformations, or portions thereof, and identifying an average location for each atom. Bound conformations in a group to be averaged can be overlayed relative to a single member or relative to a centroid position for each atom. Algorithms for determining an average structure are known in the art and include for example the OVERLAY routine in INSIGHT98 (Molecular Simulations Inc., San Diego Calif.).

The format of a ligand conformer model can be chosen based on the method used to generate the model and the desired use of the model. In this regard, a conformer model can be represented as a single structure. The resulting structure can be a unique structure compared to the conformations of the ligand bound to polypeptides in a cluster from which it was derived. Thus, the conformer model can be a new structure never before observed in nature. A model represented by a single structure can be useful for making visual comparisons by overlaying other structures with the model. A conformer model can also be represented as a plurality of structures incorporating all or a subset of the bound conformations of the ligand bound to polypeptides in a cluster. A model represented by multiple structures can be useful for identifying a range of minor deviations in the model.

In yet another representation, the conformer model can be a volume surrounding all or a subset of the bound conformations of a ligand bound to polypeptides in a cluster. A model showing volume can be useful for comparing other structures in a fitting format such that a structure which fits within the volume of the model can be identified as substantially similar to the model. One approach that can be used to fit a structure to a volume is comparison of equivalent surface patches using gnomonic projection as described for example in Chau and Dean, J. Mol. Graphics 7:130 (1989). Use of a gnomonic projection to compare structures is also described in Doucet and Weber, Computer-Aided Molecular Desicrn: Theory and ADDlications, Academic Press, San Diego Calif. (1996). Algorithms which can be used to fit a structure to a volume are known in the art and include, for example, CATALYST (Molecular Simulations Inc., San Diego, Calif.) and THREEDOM which is a part of the INTERCHEM package which makes use of an Icosahedral Matching Algorithm (Bladon, J. Mol. Graphics 7:130 (1989)) for the comparison and alignment of structures. Methods of identifying a binding compound by searching a database of structures using a gnomonic projection are described, for example, in U.S. patent application Ser. No. 09/753,020, which is hereby incorporated by reference.

A conformer model can be useful in querying a database of polypeptide structures to find other members of a polypeptide pharmacofamily. For example, a member of a polypeptide pharmacofamily can be identified by querying a database of bound conformations of a ligand to identify a retrieved bound conformation of a ligand that is substantially similar to the query structure, thereby identifying a polypeptide bound to the retrieved bound conformation as a member of the same pharmacofamily as a polypeptide bound to the query bound conformation. A conformer model can also be used to identify a new member of a polypeptide pharmacofamily by querying a database of one or more polypeptide structures using an algorithm that docks the conformer model, wherein a favorable docking result with a retrieved polypeptide indicates that the retrieved polypeptide is a member of the same polypeptide pharmacofamily as a polypeptide bound to the bound conformation used as a query. In the latter mode, a potential new member of a pharmacofamily from which the conformer model was derived can be identified. The database queries described above can be performed with algorithms available in the art including, for example, THREEDOM and CATALYST. Membership can be confirmed by using sequence based clustering methods described above for a sequence comparison signature of the amino acid sequence of the new member compared to amino acid sequence of other members of the group.

An advantage of the invention is that a conformer model can be used to identify a binding compound that is specific for polypeptides of a pharmacofamily. For example, the conformer model can be compared to a structure of a compound or to a bound conformation of a ligand to identify those having similar conformation. A conformer model can be further used to query a database of compounds to identify individual compounds having similar conformations.

A conformer model of the invention can also be used to design a binding compound that is specific for polypeptides of one or more pharmacofamilies. The methods of the invention provide a conformer model that can be produced according to a cluster of bound conformations of a ligand that are specific for polypeptides of a pharmacofamily. A conformer model identified by these criteria can be used as a scaffold structure for developing a compound having enhanced binding affinity or specificity for polypeptides of a pharmacofamily. Such a scaffold can also be used to design a combinatorial synthesis producing a library of compounds which can be screened for enhanced binding affinity for polypeptide members of a pharmacofamily or specificity for polypeptide members of one pharmacofamily compared to polypeptide members of another pharmacofamily. An algorithm can be used to design a binding compound based on a conformer model including, for example, LUDI as described by Bohm, *J. Comput. Aided Mol. Des.* 6:61–78 (1992).

A conformer model can include a portion of atoms in the bound conformations of a ligand bound to members of a pharmacofamily so long as the portion consists of contiguous atoms of a bound conformation of a ligand and provides sufficient information to distinguish one pharmacofamily from another. Thus, a conformer model can be constructed by overlaying corresponding fragments of bound conformations of a ligand and obtaining an average structure according to the methods described above. A conformer model made from a portion of a ligand can be advantageous due to its small size compared to a complete structure of the ligand from which it was derived. A conformer model based on a portion of a bound conformation of a ligand can also be used to more efficiently and rapidly query a database due to a reduced use of computer memory compared to the memory required to manipulate and store a structure containing all atoms of the ligand.

The invention provides a method for constructing a pharmacophore model. The method includes the steps of: (a) determining a sequence comparison signature for each amino acid sequence in a set of amino acid sequences, wherein the sequence comparison signature includes pairwise comparison scores for the amino acid sequence compared to each of the other amino acid sequences in the set; (b) constructing a distance arrangement including the sequence comparison signatures related according to the distance between each of the sequence comparison signatures; (c) identifying separate clusters of sequence comparison signatures in the distance arrangement, wherein the separate clusters include sequence comparison signatures for amino acid sequences in the same ligand binding family and separate pharmacofamilies; (d) comparing the bound conformations of the ligand bound to members of one of the pharmacofamilies; (e) identifying one or more conformation-dependent properties of the ligand bound to members of one of the pharmacofamilies; and (f) constructing a pharmacophore model that contains the one or more conformation-dependent properties.

A pharmacophore model can be any representation of points in a defined coordinate system that correspond to positions of atoms in a bound conformation of a ligand. For example, a point in a pharmacophore model can correlate with the center of an atom in a conformer model. An atom of a conformer model can also be represented by a series of points forming a line, plane or sphere. A line, plane or sphere can form a geometric representation designating, for example, shape of one or more atoms or volume occupied by one or more atoms.

A pharmacophore model can be represented in any coordinate system including, for example, a 2 dimensional Cartesian coordinate system or 3 dimensional Cartesian coordinate system. Other coordinate systems that can be used include a fractional coordinate system or reciprocal space such as those used in crystallographic calculations which are described in Stout and Jensen, supra.

In addition to a geometric description of a bound conformation of a ligand, a pharmacophore model can include other characteristics of atoms or moieties of the ligand including, for example, charge or hydrophobicity. Thus, a pharmacophore model can be a generalized structure, which includes but does not unambiguously describe the bound conformations of the ligand bound to the polypeptides in the pharmacofamily from which it was derived. For example, atoms can be represented as units of charge such that an oxygen in a bound conformation of a ligand can be represented by an electronegative point in the pharmacophore model. In this example, the electronegative point in the pharmacophore model includes any electronegative atom at that particular location including, for example, an oxygen or sulfur.

A pharmacophore model can be constructed to include, in addition to characteristics of the ligand itself, characteristics of an atom or moiety that interacts with the ligand and from a bound polypeptide. Characteristics of an interacting polypeptide atom or moiety that can be included in a pharmacophore model including, for example, atomic number, volume occupied, distance from an atom of the ligand, charge, hydrophobicity, polarity, or location relative to the ligand. Methods for constructing a pharmacophore model to include interacting atoms from a polypeptide are provided in U.S. patent application Ser. No. 09/753,020, which is hereby incorporated by reference.

A characteristic included in a pharmacophore model can be incorporated into a geometric representation using any additional representation that can be correlated with the characteristic. For example, use of color or shading can be used to identify regions having characteristics such as charge, polarity, or hydrophobicity. As such, the depth of shading or color or the hue of color can be used to determine the degree of a characteristic. By way of example, a common convention used in the art is to identify regions of increased positive charge with deeper shades of blue, areas of increased negative charge with deeper shades of red and neutral regions with white. Numeric representations can also be used in a pharmacophore model including, for example, values corresponding to potential energy for an interaction, or degree of polarity.

In addition, a pharmacophore model can incorporate constraints of a physical or chemical property of the bound conformations of a ligand bound to members of a pharmacofamily. A constraint of a physical property can be, for example, a distance between two atoms, allowed torsion angle of a bond, or volume of space occupied by an atom or moiety. A constraint of a chemical property can be, for example, polarity, van der Waals interaction, hydrogen bond, ionic bond, or hydrophobic interaction. Such constraints can be included in a pharmacophore model using the representations described above.

A pharmacophore model can include bound conformations of a ligand bound to members of 2 or more pharmacofamilies. Such a pharmacophore model can be used to identify a ligand having broad specificity for two or more polypeptide pharmacofamilies. Additionally, in order to identify a ligand that can preferentially bind a first polypeptide which belongs to a first polypeptide pharmacofamily compared to a second polypeptide of a second polypeptide pharmacofamily, a pharmacophore model can incorporate constraints on geometry or any other characteristic so as to exclude a characteristic of the bound conformation of the ligand bound to the second polypeptide. For example, a geometric constraint can be a forbidden region for one or more atom of a bound conformation of a ligand. A forbidden region can be identified by overlaying two conformer models in a coordinate system and identifying a coordinate or set of coordinates differentially occupied by one or more atoms of the conformer models. A pharmacophore model incorporating a forbidden region as such will be specific for a polypeptide of one pharmacofamily over a polypeptide of a second pharmacofamily correspondent with the constraint incorporated.

An advantage of the invention is that a pharmacophore model can be created based on multiple structures of the same ligand. In comparison to a pharmacophore model derived from a single structure or different ligands, a pharmacophore model derived from multiple bound conformations of the same ligand can include a greater degree of geometric information. For example, averaging of multiple bound conformations of the same ligand can provide torsion angle constraints that are not available from a single structure and not evident from comparing different ligands.

A conformation-dependent property can be identified as any property that correlates with a bound conformation of a ligand such that a change in the bound conformation results in a change in the conformation-dependent property. Accordingly, a bound conformation of a ligand, or a portion thereof, can be a conformation-dependent property. A portion of a bound conformation of a ligand can be a contiguous fragment or a non-contiguous set of atoms or bonds. A bound conformation of a ligand, or portion thereof, can be identified by any method for determining the three dimensional structure of a ligand including as disclosed herein.

Other conformation-dependent properties include, for example, absorption and emission of heat, absorption and emission of electromagnetic radiation, rotation of polarized light, magnetic moment, spin state of electrons, or polarity, as disclosed herein, or other properties that can be identified as a spectroscopic signal. Methods known in the art for measuring changes in absorption and emission of heat that correlate with changes in bound conformation of a ligand include, for example, calorimetry. Methods known in the art for measuring changes in absorption and emission of electromagnetic radiation as they correlate with changes in bound conformation of a ligand include, for example, UV/VIS spectroscopy, fluorimetry, luminometry, infrared spectroscopy, Raman spectroscopy, resonance Raman spectroscopy, X-ray absorption fine structure spectroscopy (XAFS) and the like. A change in a bound conformation of a ligand that is correlated with a change in rotation of polarized light can be measured with circular dichroism spectroscopy or optical rotation spectroscopy. A change in magnetic moment or spin state of an electron that correlates with a change in a bound conformation can be measured, for example, with Electron paramagnetic resonance spectroscopy (EPR) or nuclear magnetic resonance spectroscopy (NMR).

When based on NMR data, a conformation-dependent property can be identified as an NMR signal including, for example, chemical shift, J coupling, dipolar coupling, cross-correlation, nuclear spin relaxation, transferred nuclear Overhauser effect, and any combination thereof. A conformation-dependent property can be identified by NMR methods in both fast and slow exchange regimes. For example, in many cases, the exchange rate of a complex between ligand and polypeptide is faster than the ligand spin relaxation rate ($1/T_{1H}$). In this situation, referred to as the "fast exchange regime," transferred nuclear Overhauser effect (NOE) experiments can be performed to measure an intra-ligand proton-proton distance (Wuthrich, *NMR of proteins and Nucleic Acids*, Wiley, New York (1986) and Gronenborn, *J. Magn. Res.* 53:423–442 (1983)). Labeling of polypeptides is not required, and the ligand polypeptide concentration ratio can be adjusted to minimize line broadening of the ligand resonances while retaining strong NOE contribution from the bound form.

In a fast exchange regime, cross-correlated relaxation measurements can also provide structural information on ligand torsion angles (Carlomagno et al., *J. Am. Chem Soc.* 121:1945–1948 (1999)). These measurements include the $^1H-^1H$ dipole-dipole cross-correlation but can be extended to other cross-correlated relaxation mechanisms involving also homo- and heteronuclear chemical shielding anisotropy relaxation, as well as quadrupolar relaxation. For most of these heteronuclear experiments, the natural abundance of the isotope can be exploited. In cases where natural abundance of the isotope measured is not sufficient, isotope enriched ligands can be obtained from commercial sources such as Isotek (Miamisburg, Ohio) or Cambridge Isotope Laboratories (Andover, Mass.) or prepared by methods known in the art. Another method to determine a conformation-dependent property of a ligand in a fast exchange regime is use of residual homo- and heteronuclear dipolar couplings in partially aligned samples (Tolman et al. *Proc. Natl. Acad. Sci. USA* 92:9279–9283 (1995)).

In the slow exchange regime, the NMR signals arising from the bound conformation of the ligand are distinguished from those of the polypeptide to reduce resonance overlap. This can be achieved with different isotope labeling schemes of polypeptide, ligand or both. For large systems, perdeuteration of macromolecules and TROSY-type experiments (Pervushkin, *Proc. Natl. Acad. Sci. USA* 94:12366–12371 (1997)) can be used to minimize signal losses due to fast transverse relaxation of the resonances of the complex. With the appropriate sample requirements and isotope filtered experiments, cross-correlations, cross-relaxations and residual dipolar couplings can be measured and provide necessary structural information.

In addition, homo- and heteronuclear two and three bond J couplings can be obtained to provide information on torsion angles (Wuthrich, supra). For example, the bound conformations of NADP bound to members of different pharmacofamilies can differ by a torsion angle defined by the atoms PN-O5'N-C5'N-C4'N as described in U.S. patent application Ser. No. 09/753,020, which is hereby incorporated by reference. These torsion angles can be measured and distinguished by measuring the three bond $^{31}$P-$^{13}$C4' J coupling constants that correspond to this torsion angle (Marino, *Acc. Chem. Res.* 32:614–623 (1999)). Basically, two $^{1}$H-$^{13}$C correlation experiments can be performed with and without 31P decoupling during $^{13}$C evolution. The intensity ratio of the $^{1}$H 4'/$^{13}$C4' cross peak from each experiment is proportional to the $^{31}$P-$^{13}$C4' J coupling constant.

Correlation of a conformation-dependent property with a bound conformation of a ligand can be achieved by any method that has sufficient sensitivity to detect changes that correlate with changes in bound conformation of a ligand. Such a correlation can be determined by measuring a conformation-dependent property for various conformations of a ligand and determining the extent of change in the signal with change in the conformation. Signal changes that correlate with changes in conformation and that are detectable with a signal to noise ratio accepted in the art as significant can be used in the invention.

Correlation between a conformation-dependent property and a conformation can be determined for a ligand bound to any partner so long as binding is specific and stable. For example, for purposes of establishing a correlation, changes in a conformation dependent property that correlate with changes in bound conformation of a ligand can be determined for a ligand bound to polypeptides from different polypeptide pharmacofamilies. A bound conformation of the ligand in each complex can be determined and a conformation-dependent property can be measured for each complex. Comparison of bound conformations of the ligand in each complex with a measured conformation-dependent property can be used to establish a correlation. Demonstration of a method for establishing a correlation between an NMR signal and bound conformations of a ligand is described in U.S. patent application Ser. No. 09/753,020, which is hereby incorporated by reference. Other methods for correlating spectroscopic signals with bound conformations of a ligand are known in the art including, for example, correlation of transferred NOE signals with anti and syn conformations of the nicotinamide ring in NADPH as described in Sem and Kasper *Biochemistry* 31:3391–3398 (1992). Correlation of transferred NOE signals with conformation is also described in Clore and Gronenborn, *J. Magn. Reson.* 48:402–417 (1982).

A correlation between a bound conformation and a conformation-dependent property can also be established for a ligand bound to a non-polypeptide binding partner because a conformation-dependent property of a ligand can be independent of interactions that differ between binding partners so long as the ligand is in the same bound conformation when bound to the binding partners. Other binding partners include, for example, nucleic acids, carbohydrates, and synthetic organometallic complexes.

The invention further provides a method for predicting the bound conformation of a ligand bound to polypeptide. The method includes the steps of: (a) determining a query sequence comparison signature for an amino acid sequence, wherein the query sequence comparison signature includes pairwise comparison scores for the amino acid sequence compared to each amino acid sequence in a set; (b) comparing the distance between the query sequence comparison signature and the sequence comparison signatures for other amino acid sequences in the set, wherein the sequence comparison signatures for other amino acid sequences in the set are clustered into pharmacofamilies; (c) identifying a proximal cluster having one or more sequence comparison signature that has a closer distance to the query sequence comparison signature than the sequence comparison signatures of a distal cluster, thereby identifying the sequences having the query sequence comparison signature as being a member of the pharmacofamily for the proximal cluster, wherein the pharmacofamilies for the proximal and distal clusters belong to the same ligand binding family; and (d) obtaining a pharmacophore model of the ligand bound to the pharmacofamily for the proximal cluster, wherein the pharmacophore model includes a prediction of the bound conformation for the ligand bound to the amino acid sequence having the query sequence comparison signature.

A pharmacophore model can be useful in querying a database of polypeptide structures to find other members of a polypeptide pharmacofamily. For example, a member of a polypeptide pharmacofamily can be identified by querying a database of bound conformations of a ligand to retrieve a structure that fits the constraints of the query pharmacophore model, thereby identifying the retrieved polypeptide as a member of the pharmacofamily from which the pharmacophore model was derived. A pharmacophore model can also be used to identify a new member of a polypeptide pharmacofamily by querying a database of one or more polypeptide structures using an algorithm that docks or compares the pharmacophore model to polypeptide structures, wherein a favorable docking or comparison identifies a polypeptide as a member of the same polypeptide pharmacofamily from which the pharmacophore model was derived. The database queries described above can be performed with algorithms available in the art including, for example, THREEDOM and CATALYST. Membership can be confirmed by using sequence based clustering methods described above for a sequence comparison signature of the amino acid sequence of the new member compared to amino acid sequence of other members of the group.

An advantage of the invention is that a pharmacophore model can also be used to identify a binding compound that is specific for polypeptides of one or more pharmacofamilies. For example, a pharmacophore model can be compared to a structure of a compound or to a bound conformation of a ligand to identify those having similar properties. A conformer model can be further used to query a database of compounds to identify individual compounds having similar properties.

A pharmacophore model of the invention can also be used to design a binding compound that is specific for polypeptides of one or more pharmacofamilies. A pharmacophore model identified by these criteria can be used as a scaffold or set of constraints for developing a compound having enhanced binding affinity or specificity for polypeptides of one or more pharmacofamilies. Using similar methods a pharmacophore model can be used to design a combinatorial synthesis producing a library of compounds having properties consistent or similar to the model which can be then be screened for enhanced binding affinity or specificity for polypeptide members of one or more pharmacofamilies. An algorithm can be used to design a binding compound based on a pharmacophore model including, for example, LUDI as described by Bohm, *J. Comput. Aided Mol. Des.* 6:61–78 (1992).

A compound can be identified as satisfying the constraints of a pharmacophore model by a variety of methods for comparing structures. For example, a pharmacophore model that is a geometric representation such as a conformer model can be overlaid with a compound, and the best fit determined as described herein. Substantial overlap between a compound and a pharmacophore model can be indicated by a visual comparison and/or computation based comparison based on for example, RMSD values or torsion angle values as described above. In a case where a pharmacophore model is represented by constraints, a compound can be fitted to the pharmacophore model to identify if the properties of the compound satisfy the constraints of the pharmacophore model. For example, if a pharmacophore model contains, as a constraint, a maximum distance between atoms, a compound that satisfies the constraint can be identified as having a bond distance between corresponding atoms that is at least the maximum value. One skilled in the art will know how to extend such methods of comparison to any physical or chemical constraint.

A compound can also be identified as satisfying the constraints of a pharmacophore model by demonstrating the same characteristics for one or more specific atom located within a volume of space defined by the geometric constraints of the pharmacophore model. For example, in a case where polarity is a constraint and where a conformation of a compound can be overlaid with a pharmacophore model, an atom that overlaps a volume of space indicated by the pharmacophore and having polarity within the defined limits can be identified as satisfying constraints of the pharmacophore. By extension, a compound having atoms which satisfy all constraints of a pharmacophore is identified as a binding compound for one or more members of a polypeptide pharmacofamily from which the pharmacophore was produced.

Furthermore, the invention provides a method for predicting the three-dimensional structure of a polypeptide. A subset of polypeptides to which a query sequence belongs can be identified as described above. A polypeptide having a sequence comparison signature in the same cluster as the sequence comparison signature for the query polypeptide and for which a three-dimensional structural model has been determined can be identified and the three dimensional structural model used as a template to construct a three dimensional model of the query polypeptide. For example, such a method can include the steps of: (a) determining a query sequence comparison signature for an amino acid sequence, wherein the query sequence comparison signature includes pairwise comparison scores for the amino acid sequence for a query polypeptide compared to each amino acid sequence in a set; (b) comparing the distance between the query sequence comparison signature and the sequence comparison signatures for other amino acid sequences in the set, wherein the sequence comparison signatures for other amino acid sequences in the set are clustered into two or more subsets; (c) identifying a proximal cluster having one or more sequence comparison signature that has a closer distance to the query sequence comparison signature than the sequence comparison signatures of a distal cluster, thereby identifying the sequences having the query sequence comparison signature as being a member of the subset for the proximal cluster; (d) identifying a polypeptide having a sequence comparison score in the proximal cluster and a three-dimensional structure model; and (e) producing a structural model of the query polypeptide using the three-dimensional structure model as a template.

A variety of methods are known in the art for modeling the three dimensional structure of a polypeptide according to the amino acid sequence of the polypeptide and a structure of a second polypeptide used as a template. Available algorithms include, for example, GRASP (Nicholls, A., supra), ALADDIN (Van Drie et al. supra), INSIGHT98 (Molecular Simulations Inc., San Diego Calif.), RASMOL (Sayle et al., *Trends Biochem Sci.* 20:374–376 (1995)) and MOLMOL (Koradi et al., *J. Mol. Graphics* 14:51–55 (1996)). Construction of a homology model for a polypeptide based on a template identified by the sequence based clustering methods of the invention is demonstrated in Example III.

A model of a polypeptide determined by the methods of the invention can be useful for identifying a function of the polypeptide. For example, residues of a polypeptide that are involved in binding can be identified using a model of the invention. Residues identified as participating in binding can be modified, for example, to engineer new functions into a polypeptide, to reduce an intrinsic activity of a polypeptide, or to enhance an intrinsic activity of a polypeptide. In another example, a model of a polypeptide can be compared to other polypeptide structures to identify similar functions. Exemplary functions that can be identified from a polypeptide structure include binding interactions with other polypeptides and catalytic activities.

The following examples are intended to illustrate but not limit the present invention.

EXAMPLE I

Sequence-Based Clustering of Polypeptides

This example describes methods for grouping polypeptides into classes of overall fold and similar characteristics in their binding sites based on relationships identified by comparing their amino acid sequences.

Each polypeptide in a set of 15 amino acid sequences was characterized by a string of scores that described its sequence similarity to every other sequence in the data set. The string of scores constitutes a descriptor or property of the polypeptide. FIG. 1 shows comparison scores for 15 sequences. The scores of FIG. 1 are percent identity scores that have been binned into 10 different groups and were computed using BLAST 2.1.2 from NCBI as described in Nicholas et al., *Biotechniques* 28:1174–1191 (2000). The values were binned into 10 groups, from 0 to 9, where sequences having a pairwise identity of less than 10% are binned into 0, those with 11–20% identity are binned into 1 and so forth up to bin 9 which contains those with identity scores of 91–100%. Accordingly, 9 indicates that the sequences are highly similar or identical, while 0 indicates there is no similarity between the two sequences. The sequence comparison signature for Sequence 1 was (9,0,0, 0,0,0,0,0,0,5,2,1,0,0,0), and the sequence comparison signature for Sequence 2 was (0,9,1,6,0,3,0,3,1,0,0,0,0,0,0).

A comparison matrix was created by measuring the Euclidian distance between each of the sequence comparison signatures shown in FIG. 1. The Euclidean distances were measured as described in Manley, *Multivariate Statistical Methods, a Primer*, Chapman Hall 1994. Groups among the 15 sequences were defined using a divisive hierarchical clustering algorithm as described in Kaufman and Rousseeuw, *Finding Groups in Data: An introduction to Cluster Analysis* John Wiley and Sons, New York (1990). FIG. 2 shows a graphical representation of the sequence comparison signatures rearranged such that three clusters are apparent. The first cluster included Sequences 1, 10, 11 and 12; the second cluster included Sequences 8, 7, 4, 3, 2 and 5; and the third cluster includes Sequences 6, 14, 13, 9 and 15.

A new sequence (Sequence 16) was compared to the clusters of FIG. 2 to identify to which cluster it belonged. A sequence comparison signature was calculated for Sequence 16 compared to the 15 sequences of the set. Comparison of the sequence comparison signature for Sequence 16 to the other 15 sequence comparison signatures is shown in FIG. 3 indicates that Sequence 16 belongs to the second cluster. Therefore, the polypeptide having Sequence 16 is predicted to share structural features of the polypeptides with Sequences 8, 7, 4, 3, 2 and 5, in particular at the binding site and to bind to the same bound conformation of a common ligand that binds at that site.

EXAMPLE II

Sequence-Based Clustering of NAD(P)-Binding Polypeptides

This example demonstrates a sequence-based method for classifying polypeptides into separate pharmacofamilies that correlate with in-class binding to similar bound conformations of a ligand and cross-class binding to different bound conformations of the ligand.

A database of NAD(P) utilizing enzymes was created primarily from sequences available in the Swiss-Prot Database. The Swiss-Prot database was found to contain 4,613 sequences for polypeptides that utilize NAD(P) to perform their enzymatic functions, which represents approximately 4.7% of the sequences in the Swiss-Prot database. The database of NAD(P) utilizing enzymes included a variety of enzymes including NAD(P)-dependent oxidoreductases, NAD(P) synthetases, ADP ribosylating toxins, NAD-dependent ligases, poly-ADP ribose polymerases, and NAD(P)-dependent deacetylases.

A comparison matrix was calculated for sequences in the database of NAD(P) utilizing enzymes and clusters were identified as described in Example I. Sequence comparison scores were calculated by the BLAST algorithm in part because it is a relatively fast algorithm that is appropriate for rapidly characterizing large sequence datasets. Three pairwise comparison metrics were evaluated using the common neighbor clustering approach: cluster analyses were performed that utilized either sequence identity scores, E-scores or bit-scores calculated by BLAST. While each strategy yielded similar results, cluster analysis using Blast bit-scores yielded 120 sequence groups, E-score yielded 135 sequence groups, and cluster analysis utilizing sequence identity scores yielded 94 sequence groups. The differences in the number of sequence groups identified for each strategy arise from division of groups derived from clustering by sequence identities into subgroups when clustered on bit-scores or E-scores. Bit scores and E-scores appear to cluster sequences into a larger number of families that display greater sequence homology compared to sequence clusters derived from pairwise sequence identities.

Because the 94 sequence clusters identified using sequence identity scores appeared to correlate with structure and pharmacofamily, this set of sequences was utilized for further analysis. Table 1 shows a list of the 94 identified sequence families (SF), where the number of sequences in each SF is provided (members), as is the number of unique structures (the value 0 indicates absence of a known structure) and catalytic functions (enzyme classifications as provided in the Expasy database). Also shown for each SF are the identity of cofactors bound by the members, identity of the NAD(P) pharmacophore common to the members of the SF, and a description or name of an exemplary enzyme in each SF. The clustering procedure segregated sequence clusters that belong to the NAD(P) ubiquinone oxidative complex, sequence clusters that correspond to enzymes catalyzing oxidation or reduction of a substrate, and sequence clusters that catalyze non-redox chemistries such as NAD(P) synthetases.

Approximately half of the sequence clusters contained only one enzyme function, while others contained sequences representing as many as 38 different catalytic mechanisms. Many sequence clusters that contained multiple enzyme functions were related by mechanism or substrates or both. For example, sequence cluster 23, composed of the disulfide dehydrogenases, contained 25 enzyme mechanisms that all utilize a coupled NAD-FAD redox reaction to reduce disulfide bonds. In several cases, a single enzymatic function or a group of highly related enzyme functions was represented in multiple sequence groups. In particular, the alcohol dehydrogenases (E.C. 1.1.1.1) were found in sequence clusters 1, 2, 20 and 50.

Sequence clustering results correlated strongly with protein fold classifications. In each case where structural information was available for multiple members of a sequence family, each structure was related by a common NAD(P) binding protein fold. In general, structures in each sequence family correlated to a single SCOP polypeptide family describing the NAD(P)-binding domain. In two instances, sequence clusters correlated to multiple polypeptide folds classified by SCOP. However, in these two instances, structural folds for polypeptides in the clusters were very similar, particularly in the regions of the polypeptide that interact with the NAD(P) cofactor.

A biologically relevant NAD(P) conformer subset was generated from NAD(P) conformations derived from structures of NAD(P) complexed to enzymes in the PDB database using the methods described in U.S. patent application Ser. Nos. 09/753,020 and 09/747,174, which are hereby incorporated by reference. Using the root mean square deviation of the NAD(P) atomic coordinates (rmsd) as a distance metric between conformers, the database was clustered into 16 NAD(P) pharmacofamilies.

As shown in Table 1, a single pharmacofamily (NAD(P) pharmacophore) identified from comparison of bound ligand structures could be correlated with many of the sequence families (SF in Table 1) that were identified from sequence based comparisons.

TABLE 1

Sequence Families of NAD-Dependent Enzymes

| SF | Members | Unique Structures | Catalyitic Functions | Cofactors | NAD(P) Pharmacophore | Enzyme Description |
|---|---|---|---|---|---|---|
| 1 | 29 | 1 | 7 | NAD(P) | Two- | Alchol dehydrogenases |
| 2 | 189 | 13 | 12 | NAD(P) | Domain | Alcohol dehydrogenases |
| 3 | 28 | 1 | 2 | NAD | Rossman | UDP/NDP/GDP-sugar DH |
| 4 | 39 | 2 | 1 | NAD | Fold | Adenosylhomocysteinase |
| 5 | 47 | 5 | 4 | NAD | 1/2 | D-3-phosphoglycerate Dehydrogenase |
| 6 | 21 | 1 | 2 | NADP | | Homoserine dehydrogenase |
| 7 | 237 | 14 | 5 | NAD(P) | | Glyceraldehyde-3-phosphate DH |

TABLE 1-continued

Sequence Families of NAD-Dependent Enzymes

| SF | Members | Unique Structures | Catalyitic Functions | Cofactors | NAD(P) Pharma-cophore | Enzyme Description |
|---|---|---|---|---|---|---|
| 8 | 133 | 19 | 3 | NAD(P) | | L-lactate/malate dehydrogenase |
| 9 | 73 | 6 | 5 | NAD(P) | | Amino acid dehydrogenases |
| 10 | 20 | 3 | 2 | NAD(P) | | C-1-tetrahydrofolate synthase |
| 11 | 24 | 2 | 6 | NAD(P) | | 3-hydroxyacyl-CoA dehydrogenase |
| 12 | 56 | 1 | 3 | NAD(P) | | Glycerol-3-phosphate DH |
| 13 | 59 | 2 | 2 | NAD(P) | | 6-phosphogluconate dehydrogenase |
| 14 | 28 | 1 | 2 | NAD(P) | | Ketol-acid reductoisomerase |
| 15 | 53 | 2 | 3 | NADP | | Glucose-6-phosphate 1-dehydrogenase |
| 16 | 29 | 1 | 1 | NADP | | Dihydrodipicolinate reductase |
| 17 | 36 | 1 | 3 | NAD(P) | | NADP-dependent malic enzyme |
| 18 | 28 | 0 | 1 | NADP | | Glucose-6-phosphate 1-dehydrogenase |
| 19 | 29 | 0 | 1 | NADP | | N-acetyl-γ-glutamyl phosphate reductase |
| 20 | 143 | 9 | 12 | NAD(P) | Single | Short-chain dehydrogenases 1 |
| 21 | 362 | 17 | 38 | NAD(P) | Domain Rossman Fold 3 | Short-chain dehydrogenases 2 |
| 22 | 3 | 0 | 1 | NADP | FMN | NAD(H)-dependent FMN reductase |
| 23 | 265 | 15 | 25 | NAD(P) | FAD, FMN | 7 | Disulfide dehydrogenases |
| 24 | 7 | 1 | 1 | NADP | FAD, FMN, Heme | 8 | Sulfite reductase |
| 25 | 148 | 18 | 14 | NAD(P) | FAD, FMN, Heme | | Cyp450 reductase/Ferredoxin reductase/NO synthase |
| 26 | 22 | 1 | 1 | NADP | FAD | | UDP-N-acetylenolpyruvoyl-glucosamine reductase |
| 27 | 8 | 0 | 1 | NADP | FAD | | Methylenetetrahydrofolate reductase |
| 28 | 8 | 1 | 2 | NAD(P) | FAD | | NADP transhydrogenase |
| 29 | 14 | 2 | 2 | NAD | FAD, Heme | 12 | Aldehyde oxidase |
| 30–31 | 29 | 2 | 5 | NAD | FAD, Heme | | Dioxygenases (subunit A and B) |
| 32 | 10 | 2 | 1 | NADP | FAD, FMN | | NAD(P)H dehydrogenase |
| 33 | 17 | 6 | 1 | NAD(P) | FAD, FMN | | NADPH-flavin oxidoreductase |
| 34–45 | 1026 | 0 | 1 | NAD | FMN | | Proteins associated with the NADH dehydrogenase, plastoquinone oxidoreductase, and ubiquinone oxidoreductase complexes |
| 46 | 10 | 3 | 1 | NADP | Heme | 4 | Catalases |
| 47 | 27 | 3 | 5 | NADP | Heme | | Cyp450/Benzoate 4-monooxygenase |
| 48 | 6 | 0 | 1 | NAD | Heme | | Siroheme synthase |
| 49 | 14 | 0 | — | NAD(P) | | | Ferric reductase |
| 50 | 36 | 7 | 13 | NADP | | 5 | Aldo-keto reductases |
| 51 | 64 | 5 | 2 | NAD(P) | | | Inosine-5'-monophosphate dehydrogenase |
| 52 | 66 | 7 | 1 | NAD(P) | | 6 | Dihydrofolate reductase |
| 53 | 118 | 8 | 5 | NAD(P) | | 9 | Isocitrate/3-isopropylmalate dehydrogenase |
| 54 | 47 | 2 | 2 | NAD(P) | | 10 | 3-hydroxy-3-methylglutaryl-CoA reductase |
| 55 | 125 | 7 | 15 | NAD(P) | | 11 | Aldehyde dehydrogenases |
| 56 | 21 | 0 | 2 | NADP | | | Gamma-glutamyl phosphate reductase |
| 57 | 4 | 4 | 1 | NAD(P) | | | NAD(P)H dehydrogenase (quinone) |

TABLE 1-continued

Sequence Families of NAD-Dependent Enzymes

| SF | Members | Unique Structures | Catalyitic Functions | Cofactors | NAD(P) Pharma-cophore | Enzyme Description |
|---|---|---|---|---|---|---|
| 58 | 35 | 1 | 4 | NAD(P) | | Shikimate 5-dehydrogenase/ Dehydroquinate synthase (multifunctional proteins) |
| 59 | 23 | 0 | 2 | NAD | | Histidinol dehydrogenase |
| 60 | 41 | 1 | 1 | NADP | | Glutamyl-tRNA reductases |
| 61 | 56 | 0 | 1 | NADP | | Light-independent protochlorophyllide reductase |
| 62 | 14 | 1 | 1 | NAD | 13 | Deoxyhypusine synthase |
| 63 | 18 | 0 | 2 | NADP | | 5-amino-6(5-phosphoribosylamino) uracil reductase |
| 64 | 6 | 0 | 1 | NAD | | Malate dehydrogenase |
| 65 | 17 | 0 | 4 | NAD | | Mannitol-1-phosphate-5-dehydrogenase |
| 66 | 6 | 0 | 1 | NADP | | Acyl-CoA reductase |
| 67 | 5 | 0 | 1 | NAD | | Myo-inositol-1-phosphate synthase |
| 68 | 4 | 0 | 2 | NADP | | D-nopaline dehydrogenase |
| 69 | 6 | 2 | 2 | NAD | | Nitrate-inducible formate dehydrogenase |
| 70 | 4 | 0 | 1 | NADP | | Precorrin-6x reductase |
| 71 | 3 | 0 | 1 | NADP | | Phosphoadenosine phosphosulfate reductase |
| 72 | 4 | 0 | 1 | NAD | | Saccharopine dehydrogenase |
| 73 | 23 | 0 | 1 | NADP | | Pyrroline-5-carboxylate reductase |
| 74 | 15 | 0 | 1 | NAD(P) | | Oxygen-independent coproporphyrinogen III oxidase |
| 75 | 5 | 0 | 1 | NADP | | L-ornithine 5-monooxygenase |
| 76 | 18 | 1 | 2 | NADP | | Acyl-[ACP] desaturase |
| 77 | 5 | 0 | 1 | NAD | | Ornithine cyclodeaminase |
| 78 | 4 | 1 | 1 | NAD | 16 | Mono-ADP-ribosyl transferase C3 precursor (botulinum) |
| 79 | 2 | 1 | 1 | NAD | | Pertussis toxin/Cholera enterotoxin precursor |
| 80 | 3 | 2 | 1 | NAD | | Exotoxin A Diptheria toxin precursor |
| 81 | 12 | 0 | 1 | NAD(P) | | NAD(P)+-arginine ADP-ribosyltransferase |
| 82 | 11 | 0 | 1 | NAD | | RNA 2'-phosphotransferase (ADP-ribosylated) |
| 83 | 10 | 1 | 1 | NAD | | Poly[ADP-ribose] polymerase |
| 84 | 5 | 1 | 1 | NAD | | ADP-ribosyl cyclase |
| 85 | 9 | 1 | 1 | NADP | | Farnesyl-diphosphate farnesyltransferase |
| 86 | 33 | 2 | 1 | NAD | 14 | Nicotinamide-nucleotide adenylyltransferase |
| 87 | 22 | 1 | 1 | NAD | | NH(3)-dependent NAD+-synthase |
| 88 | 11 | 0 | 1 | NAD | | NADH pyrophosphatase |
| 89 | 46 | 0 | 1 | NAD(P) | | Inorganic polyphosphate/ATP-NAD kinase |
| 90 | 6 | 1 | 2 | NAD | 15 | Sir2 regulatory protein |
| 91 | 31 | 2 | 1 | NAD | | DNA ligase |
| 92 | 6 | 0 | 2 | NAD | | Phosphate glucosidases |
| 93 | 5 | 0 | 2 | NAD | | Alpha-glucosidase |
| 94 | 18 | 0 | 1 | NAD | | TRK system K+ uptake protein |
| Total | 4300 | 210 | 269 | | | |

EXAMPLE III

A Three-Dimensional Homology Model for the NADPH-Binding Domain of 1-Deoxy-D-xylulose 5-phosphate reductoisomerase Based on a Template Identified by Sequence-Based Clustering This example demonstrates use of sequence-based clustering to identify a template structure for homology modeling of 1-Deoxy-D-xylulose 5-phosphate reductoisomerase (DXPR). This example further provides a homology model for the three dimensional structure of the amino terminal NADP-binding domain of DXPR. Validation of the model using nuclear magnetic resonance spectroscopy is also demonstrated.

1-Deoxy-D-xylulose 5-phosphate reductoisomerase (DXPR) is an enzyme involved in isoprenoid biosynthesis, catalyzing the formation of 2-C-methyl-D-erythritol from 1-deoxy-D-xylulose 5-phosphate (Takahashi et al., *Proc. Natl. Acad. Sci. USA* 95:9879–9884 (1998)). The deoxyxylulose pathway, found in some bacteria, algae, plants and protozoa, is an alternate to the ubiquitous mevalonate pathway for isoprenoid biosynthesis (Eisenreich et al., *Trends Plant Sci.* 6:78–84 (2001)). Because a three dimensional model of the DXPR structure was not available and to aid in the design of inhibitors of DXPR, a model for the NADPH-binding, N-terminal domain of the enzyme for *E. coli* was produced and validated as set forth below.

The *E. coli* DXPR amino acid sequence was used to search for homologs with BLAST and PSI-BLAST using default parameters. Neither algorithm identified homologous sequences below an E-score of 0.005 in the Swiss-Prot database (other than orthologues of DXPR). Other methods such as SDSC1 (Shindyalov and Bourne, *Fourth Meeting on the Critical Assessment of Techniques for Protein Structure Prediction*, A-92 (2000)) and 3D-JIGSAW (Bates and Sternberg, *Proteins: Structure, Function and Genetics* Suppl. 3:47–54 (1999)) were also unable to identify homologues for potential use as templates. The threading server 3D-PSSM (Kelley et al., *J. Mol. Biol.* 299:499–520 (2000)), also did not identify any hits below a significant E-value.

Sequence comparison signatures were determined for the NAD(P)-binding sequences (including 28 DXPR sequences) in the Swiss-Prot database and clustering was performed as described in Examples I and II. The 28 DXPR sequences formed one cluster. When visualized in a comparison matrix, the DXPR cluster was proximal to other clusters. These other clusters were composed of aspartate semialdehyde dehydrogenase, homoserine dehydrogenase, N-acetyl-g-glutamyl phosphate reductoisomerase, or glyceraldehyde 3-phosphate dehydrogenase; all of which share a common NAD(P)-binding Rossmann fold. The proximity correlated with local sequence identity between DXPR sequences and sequences of these other clusters, ranging from about 17 to 40% local sequence identity. Although the E-scores of these sequence identities were between 0.1 and 2.0, these clusters were identified as related groups because multiple DXPR sequences systematically showed cross-talk to only the above mentioned sequence clusters. In particular, cross-talk was identified as low sequence identity (less than 30%) between the cluster containing DXPR and a few sequences belonging to other clusters, which showed a pattern that was distinct from a pattern observed in the cluster. The cross talk was distinguishable from true noise because in the case of noise, only a single DXPR sequence had low similarity to some other cluster. Based on these data, the NADP-binding domain of *E. coli* DXPR was predicted to contain a Rossmann fold.

The local sequence identities between the sequences in the proximal clusters occurred in the N-terminal, NAD(P)-binding domain. In order to choose a template for homology modeling of the DXPR NAD(P)-binding domain, the sequences in the other clusters were evaluated according to their proximity to DXPR in the sequence comparison matrix and whether or not a structural model was available for members of the cluster. Homoserine dehydrogenase and aspartate semialdehyde dehydrogenase showed the most proximity to DXPR in the sequence comparison matrix. Of these two, a crystal structure was available for homoserine dehydrogenase.

A multiple-alignment of *E. coil* DXPR with the NAD-binding domain of *S. cerevisiae* homoserine dehydrogenase was performed using Clustaiw (Thompson et al., *Nucl. Acids. Res.* 22:4673–4680 (1994)). The NAD-binding motif of *E. coli* DXPR (LGXTGSIG; SEQ ID NO:3) aligned very well with the NAD-binding motif of *S. cerevisiae* homoserine dehydrogenase (IGAGVVGS; SEQ ID NO:4) as shown in FIG. 4. This alignment was used to build several models of *E. coli* DXPR using the MODELER module in MSI Insight II (Sali and Blundell, *J. Mol. Biol.* 234:779–815 (1993)). The model having the least coiling of loops was chosen and is shown in FIG. 5, with some NADP-contact residues colored in blue (isoleucine), black (methionine), and cyan (lysine). The bound conformation of NAD from homoserine dehydrogenase is superimposed on the model and shown in green.

The validity of the homology model was tested using nuclear magnetic resonance (NMR) spectroscopy. Based on proton chemical shifts, it was possible to observe changes in the chemical environment around NADPH and thereby determine which residues in the polypeptide were interacting with the coenzyme. Nuclear Overhauser Effect peaks (NOE's) observed between NADPH and residues in the binding pocket of *E. coli* DXPR were consistent with those in the homology model in that methionine, isoleucine and lysine residues were observed to be in proximity of the cofactor. Thus, the model satisfied the constrains observed by NMR spectroscopy.

Throughout this application various publications have been referenced. The disclosures of these publications in their entireties are hereby incorporated by reference in this application in order to more fully describe the state of the art to which this invention pertains.

Although the invention has been described with reference to the examples provided above, it should be understood that various modifications can be made without departing from the spirit of the invention. Accordingly, the invention is limited only by the claims.

---

What is claimed is:

1. A method for separating two or more subsets of polypeptides within a set of polypeptides, comprising:
   (a) determining a sequence comparison signature for each amino acid sequence in a set of amino acid sequences, wherein said sequence comparison signature comprises pairwise comparison scores for said amino acid sequence compared to each of the other amino acid sequences in said set;
   (b) constructing a distance arrangement comprising said sequence comparison signatures related according to the distance between each of said sequence comparison signatures; and
   (c) identifying a first and second cluster of sequence comparison signatures in the distance arrangement, wherein said first cluster comprises sequence comparison signatures for polypeptides having a similar protein fold or biological function, said protein fold or function being different compared to a protein fold or function of polypeptides having sequence comparison signatures in said second cluster, wherein said pairwise comparison score is determined by an algorithm selected from the group consisting of Smith-Waterman, BLAST, FASTA, Needleman-Wunach, Seller and PSI-BLAST.

2. A method for separating two or more subsets of polypeptides within a set of polypeptides, comprising:
   (a) determining a sequence comparison signature for each amino acid sequence in a set of amino acid sequences, wherein said sequence comparison signature comprises pairwise comparison scores for said amino acid sequence compared to each of the other amino acid sequences in said set;
   (b) constructing a distance arrangement comprising said sequence comparison signatures related according to the distance between each of said sequence comparison signatures; and
   (c) identifying a first and second cluster of sequence comparison signatures in the distance arrangement, wherein said first cluster comprises sequence comparison signatures for polypeptides having a similar protein fold or biological function, said protein fold or function being different compared to a protein fold or function of polypeptides having sequence comparison signatures in said second cluster, wherein said distance comprises a distance selected from the group consisting of a Euclidian distance, exclusive OR distance and Tanimoto coefficient.

3. A method for seperating two or more subsets of polypeptides within a set of polypeptides, comprising:
   (a) determining a sequence comparison signature for each amino acid sequence in a set of amino acid sequences, wherein said sequence comparison signature comprises pairwise comparison scores for said amino acid sequence compared to each of the other amino acid sequences in said set;
   (b) constructing a distance arrangement comprising said sequence comparison signatures related according to the distance between each of said sequence comparison signatures; and
   (c) identifying a first and second cluster of sequence comparison signatures in the distance arrangement, wherein said first cluster comprises sequence comparison signatures for polypeptides having a similar protein fold or biological function, said protein fold or function being different compared to a protein fold or function of polypeptides having sequence comparison signatures in said second cluster, wherein said distance comprises a distance selected from the group consisting of a Penrose distance and Mahalanobis distance.

4. A method for separating two or more subsets of polypeptides within a set of polypeptides, comprising:
   (a) determining a sequence comparison signature for each amino acid sequence in a set of amino acid sequences, wherein said sequence comparison signature comprises pairwise comparison scores for said amino acid sequence compared to each of the other amino acid sequences in said set;
   (b) constructing a distance arrangement comprising said sequence comparison signatures related according to the distance between each of said sequence comparison signatures; and
   (c) identifying a first and second cluster of sequence comparison signatures in the distance arrangement, wherein said first cluster comprises sequence comparison signatures for polypeptides having a similar protein fold or biological function, said protein fold or function being different compared to a protein fold or function of polypeptides having sequence comparison signatures in said second cluster, wherein said cluster of sequence comparison signatures is identified by hierarchical clustering wherein said hierarchical clustering is selected from the group consisting of agglomerative clustering and divisive clustering.

5. A method for separating two or more subsets of polypeptides within a set of polypeptides, comprising:

(a) determining a sequence comparison signature for each amino acid sequence in a set of amino acid sequences, wherein said sequence comparison signature comprises pairwise comparison scores for said amino acid sequence compared to each of the other amino acid sequences in said set;

(b) constructing a distance arrangement comprising said sequence comparison signatures related according to the distance between each of said sequence comparison signatures; and (c) identifying a first and second cluster of sequence comparison signatures in the distance arrangement, wherein said first cluster comprises sequence comparison signatures for polypeptides having a similar protein fold or biological function, said protein fold or function being different compared to a protein fold or function of polypeptides having sequence comparison signatures in said second cluster, wherein said cluster of sequence comparison signatures is identified by non-hierarchical clustering.

6. The method of claim 5, wherein said non-hierarchical clustering comprises Jarvis-Patrick clustering.

7. A method for seperating two or more subsets of polypeptides within a set of polypeptides, comprising:

(a) determining a sequence comparison signature for each amino acid sequence in a set of amino acid sequences, wherein said sequence comparison signature comprises pairwise comparison scores for said amino acid sequence compared to each of the other amino acid sequences in said set;

(b) constructing a distance arrangement comprising said sequence comparison signatures related according to the distance between each of said sequence comparison signatures; and (c) identifying a first and second cluster of sequence comparison signatures in the distance arrangement, wherein said first cluster comprises sequence comparison signatures for polypeptides having a similar protein fold or biological function, said protein fold or function being different compared to a protein fold or function of polypeptides having sequence comparison signatures in said second cluster, wherein said cluster of sequence comparison signatures is identified by cell-based clustering.

8. A method for identifying a member of a polypeptide family, comprising:

(a) determining a query sequence comparison signature for an amino acid sequence, wherein said query sequence comparison signature comprises pairwise comparison scores for said amino acid sequence compared to each amino acid sequence in a set;

(b) comparing the distance between said query sequence comparison signature and the sequence comparison signatures for other amino acid sequences in said set, wherein said sequence comparison signatures for other amino acid sequences in said set are clustered into polypeptide families; and (c) identifying a proximal cluster having one or more sequence comparison signature that has a closer distance to said query sequence comparison signature than the sequence comparison signatures of a distal cluster, thereby identifying the polypeptide having said query sequence comparison signature as being a member of the polypeptide family for the proximal cluster.

9. The method of claim 8, wherein said pairwise comparison score is determined by an algorithm selected from the group consisting of Smith-Waterman, BLAST, FASTA, Needleman-Wunsch, Seller and PSI-BLAST.

10. The method of claim 8, wherein said distance comprises a distance selected from the group consisting of a Euclidian distance, exclusive OR distance and Tanimoto coefficient.

11. The method of claim 8, wherein said distance comprises the distance between a sequence comparison signature and a set of sequence comparison signatures.

12. The method of claim 8, wherein said distance comprises a distance selected from the group consisting of a Penrose distance and Mahalanobis distance.

13. The method of claim 8, wherein said cluster of sequence comparison signatures is identified by hierarchical clustering.

14. The method of claim 13, wherein said hierarchical clustering is selected from the group consisting of agglomerative clustering and divisive clustering.

15. The method of claim 8, wherein said cluster of sequence comparison signatures is identified by non-hierarchical clustering.

16. The method of claim 15, wherein said non-hierarchical clustering comprises Jarvis-Patrick clustering.

17. The method of claim 8, wherein said cluster of sequence comparison signatures is identified by cell-based clustering.

18. The method of claim 8, wherein said polypeptide family comprises polypeptides having a common structural fold.

19. The method of claim 8, wherein said polypeptide family comprises polypeptides having a common function.

20. A method for identifying a polypeptide pharmacofamily, comprising:

(a) determining a sequence comparison signature for each amino acid sequence in a set of amino acid sequences, wherein said sequence comparison signature comprises pairwise comparison scores for said amino acid sequence compared to each of the other amino acid sequences in said set;

(b) constructing a distance arrangement comprising said sequence comparison signatures related according to the distance between each of said sequence comparison signatures; and (c) identifying separate clusters of sequence comparison signatures in said distance arrangement, wherein said separate clusters comprise sequence comparison signatures for sequences in the same ligand binding family and separate pharmacofamilies.

21. The method of claim 20, wherein said pairwise comparison score is determined by an algorithm selected from the group consisting of Smith-Waterman, BLAST, FASTA, Needleman-Wunsch, Seller and PSI-BLAST.

22. The method of claim 20, wherein said distance comprises a distance selected from the group consisting of a Euclidian distance, exclusive OR distance and Tanimoto coefficient.

23. The method of claim 20, wherein said distance comprises the distance between a sequence comparison signature and a set of sequence comparison signatures.

24. The method of claim 20, wherein said distance comprises a distance selected from the group consisting of a Penrose distance and Mahalanobis distance.

25. The method of claim 20, wherein said cluster of sequence comparison signatures is identified by hierarchical clustering.

26. The method of claim 25, wherein said hierarchical clustering is selected from the group consisting of agglomerative clustering and divisive clustering.

27. The method of claim 20, wherein said cluster of sequence comparison signatures is identified by non-hierarchical clustering.

28. The method of claims wherein said non-hierarchical clustering comprises Jarvis-Patrick clustering.

29. The method of claim 20, wherein said cluster of sequence comparison signatures is identified by cell-based clustering.

30. The method of claim 20, wherein said ligand comprises a nicotinamide adenine dinucleotide-related molecule.

31. The method of claim 30, wherein said nicotinamide adenine dinucleotide-related molecule is selected from the group consisting of oxidized nicotinamide adenine dinucleotide, reduced nicotinamide adenine dinucleotide, oxidized nicotinamide adenine dinucleotide phosphate, reduced nicotinamide adenine dinucleotide phosphate, and a mimetic thereof.

32. A method for identifying a member of a pharmacofamily, comprising:
  (a) determining a query sequence comparison signature for an amino acid sequence, wherein said query sequence comparison signature comprises pairwise comparison scores for said amino acid sequence compared to each amino acid sequence in a set;
  (b) comparing the distance between said query sequence comparison signature and the sequence comparison signatures for other amino acid sequences in said set, wherein said sequence comparison signatures for other amino acid sequences in said set are clustered into pharmacofamilies; and
  (c) identifying a proximal cluster having one or more sequence comparison signature that has a closer distance to said query sequence comparison signature than the sequence comparison signatures of a distal cluster, thereby identifying the sequences having said query sequence comparison signature as being a member of the pharmacofamily for the proximal cluster, wherein the pharmacofaniilies for the proximal and distal clusters belong to the same ligand binding family.

33. The method of claim 32, wherein said pairwise comparison score is determined by an algorithm selected from the group consisting of Smith-Watennan, BLAST, FASTA, Needleman-Wunsch, Seller and PSI-BLAST.

34. The method of claim 32, wherein said distance comprises a distance selected from the group consisting of a Euclidian distance, exclusive OR distance and Tanimoto coefficient.

35. The method of claim 32, wherein said distance comprises the distance between a sequence comparison signature and a set of sequence comparison signatures.

36. The method of claim 35, wherein said distance comprises a distance selected from the group consisting of a Penrose distance and Mahalanobis distance.

37. The of claim 32, wherein said cluster of sequence comparison signatures is identified by hierarchical clustering.

38. The method of claim 37, wherein said hierarchical clustering is selected from the group consisting of agglomerative clustering and divisive clustering.

39. The method of claim 37, wherein said cluster of sequence comparison signatures is identified by non-hierarchical clustering.

40. The method of claim 39, wherein said non-hierarchical clustering comprises Jarvis-Patrick clustering.

41. The method of claim 32, wherein said cluster of sequence comparison signatures is identified by cell-based clustering.

42. The method of claim 32, wherein said ligand comprises a nicotinamide adenme dinucleotide-related molecule.

43. The method of claim 42, wherein said nicotinamide adenine dinucleotide-related molecule is selected from the group consisting of oxidized nicotinamide adenine dinucleotide, reduced nicotinamide adenine dinucleotide, oxidized nicotinamide adenine dinucleotide phosphate, reduced nicotinamide adenine dinucleotide phosphate, and a mimetic thereof.

44. A method for constructing a conformer model, comprising:
  (a) determining a sequence comparison signature for each amino acid sequence in a set of amino acid sequences, wherein said sequence comparison signature comprises pairwise comparison scores for said amino acid sequence compared to each of the other amino acid sequences in said set;
  (b) constructing a distance arrangement comprising said sequence comparison signatures related according to the distance between each of said sequence comparison signatures;
  (c) identifying separate clusters of sequence comparison signatures in said distance arrangement, wherein said separate clusters include sequence comparison signatures for amino acid sequences in the same ligand binding family and separate pharmacofamilies;
  (d) determining bound conformations of said ligand bound to the members of a pharmacofamily; and
  (e) constructing an average structure of said bound conformations, wherein said average structure is a conformer model of said ligand.

45. The method of claim 44, wherein said pairwise comparison score is determined by an algorithm selected from the group consisting of Smith-Waterman, BLAST, FASTA, Needleman-Wunsch, Seller and PSI-BLAST.

46. The method of claim 44, wherein said distance comprises a distance selected from the group consisting of a Euclidian distance, exclusive OR distance and Tanimoto coefficient.

47. The method of claim 44, wherein said distance comprises the distance between a sequence comparison signature and a set of sequence comparison signatures.

48. The method of claim 47, wherein said distance comprises a distance selected from the group consisting of a Penrose distance and Mahalanobis distance.

49. The method of claim 44, wherein said cluster of sequence comparison signatures is identified by hierarchical clustering.

50. The method of claim 49, wherein said hierarchical clustering is selected from the group consisting of agglomerative clustering and divisive clustering.

51. The method of claim 44, wherein said cluster of sequence comparison signatures is identified by non-hierarchical clustering.

52. The method of claim 51, wherein said non-hierarchical clustering comprises Jarvis-Patrick clustering.

53. The method of claim 44, wherein said cluster of sequence comparison signatures is identified by cell-based clustering.

54. The method of claim 44, wherein said ligand comprises a nicotinamide adenine dinucleotide-related molecule.

55. The method of claim 54, wherein said nicotinamide adenine dinucleotide-related molecule is selected from the group consisting of oxidized nicotinamide adenine dinucleotide, reduced nicotinamide adenine dinucleotide, oxidized nicotinamide adenine dinucleotide phosphate, reduced nicotinamide adenine dinucleotide phosphate, and a mimetic thereof.

56. A method for constructing a pharmacophore model, comprising:

(a) determining a sequence comparison signature for each amino acid sequence in a set of amino acid sequences, wherein said sequence comparison signature comprises pairwise comparison scores for said amino acid sequence compared to each of the other amino acid sequences in said set;

(b) constructing a distance arrangement comprising said sequence comparison signatures related according to the distance between each of said sequence comparison signatures;

(c) identifying separate clusters of sequence comparison signatures in said distance arrangement, wherein said separate clusters comprise sequence comparison signatures for amino acid sequences in the same ligand binding family and separate pharmacofamilies;

(d) comparing the bound conformations of said ligand bound to members of one of said pharmacofamilies;

(e) identifying one or more conformation-dependent properties of said ligand bound to members of one of said pharmacofamilies; and (f) constructing a pharmacophore model that contains said one or more conformation-dependent properties.

57. The method of claim 56, wherein said pairwise comparison score is determined by an algorithm selected from the group consisting of Smith-Watennan, BLAST, FASTA, Needleman-Wunsch, Seller and PSI-BLAST.

58. The method of claim 56, wherein said distance comprises a distance selected from the group consisting of a Euclidian distance, exclusive OR distance and Tanimoto coefficient.

59. The method of claim 56 wherein said distance comprises the distance between a sequence comparison signature and a set of sequence comparison signatures.

60. The method of claim 59, wherein said distance comprises a distance selected from the group consisting of a Penrose distance and Mahalanobis distance.

61. The method of claim 56, wherein said cluster of sequence comparison signatures is identified by hierarchical clustering.

62. The method of claim 61, wherein said hierarchical clustering is selected from the group consisting of agglomerative clustering and divisive clustering.

63. The method of claim 56, wherein said cluster of sequence comparison signatures is identified by non-hierarchical clustering.

64. The method of claim 63, wherein said non-hierarchical clustering comprises Jarvis-Patrick clustering.

65. The method of claim 56, wherein said cluster of sequence comparison signatures is identified by cell-based clustering.

66. The method of claim 56, wherein said ligand comprises a nicotinamide adenine dinucleotide-related molecule.

67. The method of claim 66, wherein said nicotinamide adezune dinucleotide-related molecule is selected from the group consisting of oxidized nicotinamide adenine dinucleotide, reduced nicotinamide adenine dinucleotide, oxidized nicotinamide adenine dinucleotide phosphate, reduced nicotinamide adenine dinucleotide phosphate, and a mimetic thereof.

68. The method of claim 67, wherein said conformation-dependent property comprises a spectroscopic signal.

69. The method of claim 67, wherein said conformation-dependent property comprises an NMR signal.

70. The method of claim 69, wherein said NMR signal is selected from the group consisting of chemical shift, J coupling, dipolar coupling, cross-correlation, nuclear spin relaxation, transferred nuclear overhauser effect, and any combination thereof.

71. A method for predicting the bound conformation of a ligand bound to polypeptide, comprising:

(a) determining a query sequence comparison signature for an amino acid sequence, wherein said query sequence comparison signature comprises pairwise comparison scores for said amino acid sequence compared to each amino acid sequence in a set;

(b) comparing the distance between said query sequence comparison signature and the sequence comparison signatures for other amino acid sequences in said set, wherein said sequence comparison signatures for other amino acid sequences in said set are clustered into pharmacofamilies;

(c) identifying a proximal cluster having one or more sequence comparison signature that has a closer distance to said query sequence comparison signature than the sequence comparison signatures of a distal cluster, thereby identifying the sequences having said query sequence comparison signature as being a member of the pharmacofamily for the proximal cluster, wherein the pharmacofamilies for the proximal and distal clusters belong to the same ligand binding family; and (d) obtaining a pharmacophore model of said ligand bound to said pharmacofamily for the proximal cluster, wherein said pharmacophore model comprises a prediction of the bound conformation for said ligand bound to the amino acid sequence having said query sequence comparison signature.

72. The method of claim 71, wherein said pairwise comparison score is determined by an algorithm selected from the group consisting of Smith-Waterman, BLAST, FASTA, Needleman-Wunsch, Seller and PSI-BLAST.

73. The method of claim 71, wherein said distance comprises a distance selected from the group consisting of a Euclidian distance, exclusive OR distance and Tanirnoto coefficient.

74. The method of claim 71, wherein said distance comprises the distance between a sequence comparison signature and a set of sequence comparison signatures.

75. The method of claim 74, wherein said distance comprises a distance selected from the group consisting of a Penrose distance and Mahalanobis distance.

76. The method of claim 71, wherein said cluster of sequence comparison signatures is identified by hierarchical clustering.

77. The method of claim 76, wherein said hierarchical clustering is selected from the group consisting of agglomerative clustering and divisive clustering.

78. The method of claim 71, wherein said cluster of sequence comparison signatures is identified by non-hierarchical clustering.

79. The method of claim 78, wherein said non-hierarchical clustering comprises Jarvis-Patrick clustering.

80. The method of claim 71, wherein said cluster of sequence comparison signatures is identified by cell-based clustering.

81. The method of claim 71, wherein said ligand comprises a nicotinamide adenine dinucleotide-related molecule.

82. The method of claim 81, wherein said nicotinamide adenine dinucleotide-related molecule is selected from the group consisting of oxidized nicotinamide adenine dinucleotide, reduced nicotinamide adenine dinucleotide, oxidized nicotinamide adenine dinucleotide phosphate, reduced nicotinamide adenine dinucleotide phosphate, and a mimetic thereof.

* * * * *

UNITED STATES PATENT AND TRADEMARK OFFICE
CERTIFICATE OF CORRECTION

PATENT NO.    : 6,792,355 B2
DATED         : September 14, 2004
INVENTOR(S)   : Hansen, Mark R. et al.

It is certified that error appears in the above-identified patent and that said Letters Patent is hereby corrected as shown below:

Column 44,
Line 1, please delete "adenme" and replace therefor with -- adenine --.

Column 45,
Line 62, please delete "adezune" and replace therefor with -- adenine --.

Column 46,
Line 8, please delete "overhauser" and replace therefor with -- Overhauser --.
Line 46, please delete "Tanirnoto" and replace therefor with -- Tanimoto --.

Signed and Sealed this

First Day of February, 2005

JON W. DUDAS
*Director of the United States Patent and Trademark Office*

SEQUENCE LISTING

<160> NUMBER OF SEQ ID NOS: 4

<210> SEQ ID NO 1
<211> LENGTH: 177
<212> TYPE: PRT
<213> ORGANISM: E. coli

<400> SEQUENCE: 1

Met Lys Gln Leu Thr Ile Leu Gly Ser Thr Gly Ser Ile Gly Cys Ser
 1               5                  10                  15

-continued

```
Thr Leu Asp Val Val Arg His Asn Pro Glu His Phe Arg Val Val Ala
             20                  25                  30

Leu Val Ala Gly Lys Asn Val Thr Arg Met Val Glu Gln Cys Leu Glu
         35                  40                  45

Phe Ser Pro Arg Tyr Ala Val Met Asp Asp Glu Ala Ser Ala Lys Leu
     50                  55                  60

Leu Lys Thr Met Leu Gln Gln Gly Ser Arg Thr Glu Val Leu Ser
 65                  70                  75                  80

Gly Gln Gln Ala Ala Cys Asp Met Ala Ala Leu Glu Asp Val Asp Gln
                 85                  90                  95

Val Met Ala Ala Ile Val Gly Ala Ala Gly Leu Leu Pro Thr Leu Ala
                100                 105                 110

Ala Ile Arg Ala Gly Lys Thr Ile Leu Leu Ala Asn Lys Glu Ser Leu
            115                 120                 125

Val Thr Cys Gly Arg Leu Phe Met Asp Ala Val Lys Gln Ser Lys Ala
        130                 135                 140

Gln Leu Leu Pro Val Asp Ser Glu His Asn Ala Ile Phe Gln Ser Leu
145                 150                 155                 160

Pro Gln Pro Ile Gln His Asn Leu Gly Tyr Ala Asp Leu Glu Gln Asn
                165                 170                 175

Gly
```

<210> SEQ ID NO 2
<211> LENGTH: 147
<212> TYPE: PRT
<213> ORGANISM: S. aureas

<400> SEQUENCE: 2

```
Ser Thr Lys Val Val Asn Val Ala Val Ile Gly Ala Gly Val Val Gly
  1               5                  10                  15

Ser Ala Phe Leu Asp Gln Leu Leu Ala Met Lys Ser Thr Ile Thr Tyr
             20                  25                  30

Asn Leu Val Leu Leu Ala Glu Ala Glu Arg Ser Leu Ile Ser Lys Asp
         35                  40                  45

Phe Ser Pro Leu Asn Val Gly Ser Asp Trp Lys Ala Ala Leu Ala Ala
     50                  55                  60

Ser Thr Thr Lys Thr Leu Pro Leu Asp Asp Leu Ile Ala His Leu Lys
 65                  70                  75                  80

Thr Ser Pro Lys Pro Val Ile Leu Val Asp Asn Thr Ser Ser Ala Tyr
                 85                  90                  95

Ile Ala Gly Phe Tyr Thr Lys Phe Val Glu Asn Gly Ile Ser Ile Ala
                100                 105                 110

Thr Pro Asn Lys Lys Ala Phe Ser Ser Asp Leu Ala Thr Trp Lys Ala
            115                 120                 125

Leu Phe Ser Asn Lys Pro Thr Asn Gly Phe Val Tyr His Glu Ala Thr
        130                 135                 140

Val Gly Ala
145
```

<210> SEQ ID NO 3
<211> LENGTH: 8
<212> TYPE: PRT
<213> ORGANISM: E. coli
<220> FEATURE:
<221> NAME/KEY: VARIANT
<222> LOCATION: 3
<223> OTHER INFORMATION: Xaa=any amino acid -continued

```
<400> SEQUENCE: 3

Leu Gly Xaa Thr Gly Ser Ile Gly
 1               5

<210> SEQ ID NO 4
<211> LENGTH: 8
<212> TYPE: PRT
<213> ORGANISM: S. cerevisiae

<400> SEQUENCE: 4

Ile Gly Ala Gly Val Val Gly Ser
 1               5
```